United States Patent
Bridgeman

(10) Patent No.: US 11,530,386 B2
(45) Date of Patent: Dec. 20, 2022

(54) CELLS EXPRESSING RECOMBINANT GROWTH FACTOR RECEPTORS

(71) Applicant: INSTIL BIO (UK) LIMITED, Manchester (GB)

(72) Inventor: John Stephen Bridgeman, Manchester (GB)

(73) Assignee: INSTIL BIO (UK) LIMITED, Manchester (GB)

( * ) Notice: Subject to any disclaimer, the term of this patent is extended or adjusted under 35 U.S.C. 154(b) by 693 days.

(21) Appl. No.: 16/061,435

(22) PCT Filed: Dec. 15, 2016

(86) PCT No.: PCT/GB2016/053949
§ 371 (c)(1),
(2) Date: Jun. 12, 2018

(87) PCT Pub. No.: WO2017/103596
PCT Pub. Date: Jun. 22, 2017

(65) Prior Publication Data
US 2020/0263130 A1    Aug. 20, 2020

(30) Foreign Application Priority Data

Dec. 15, 2015  (GB) .................................. 1522097

(51) Int. Cl.
| C07K 14/705 | (2006.01) |
| C12N 5/00 | (2006.01) |
| C07K 14/71 | (2006.01) |
| C12N 5/0783 | (2010.01) |
| A61K 35/17 | (2015.01) |
| C12N 15/86 | (2006.01) |

(52) U.S. Cl.
CPC ............ *C12N 5/0636* (2013.01); *A61K 35/17* (2013.01); *C07K 14/71* (2013.01); *C12N 15/86* (2013.01); *C12N 2510/00* (2013.01); *C12N 2740/15043* (2013.01)

(58) Field of Classification Search
CPC ..... C07K 14/705; C07K 14/71; C12N 5/0634
See application file for complete search history.

(56) References Cited

U.S. PATENT DOCUMENTS

| 5,498,599 | A | * | 3/1996 | Choi et al. ............. C12N 15/18 |
| | | | | 514/12 |
| 8,034,334 | B2 | | 10/2011 | Dudley et al. |
| 8,287,857 | B2 | | 10/2012 | Dudley et al. |
| 8,383,099 | B2 | | 2/2013 | Dudley et al. |
| 8,809,050 | B2 | | 8/2014 | Vera et al. |
| 8,956,860 | B2 | | 2/2015 | Vera et al. |
| 9,074,185 | B2 | | 7/2015 | Dudley et al. |
| 9,567,565 | B2 | | 2/2017 | Vera et al. |
| 9,844,569 | B2 | | 12/2017 | Gros et al. |
| 10,130,659 | B2 | | 11/2018 | Wardell et al. |
| 10,166,257 | B2 | | 1/2019 | Wardell et al. |
| 10,272,113 | B2 | | 4/2019 | Wardell et al. |
| 10,363,273 | B2 | | 7/2019 | Wardell et al. |
| 10,398,734 | B2 | | 9/2019 | Wardell et al. |
| 10,415,015 | B2 | | 9/2019 | Veerapathran et al. |
| 10,420,799 | B2 | | 9/2019 | Wardell et al. |
| 10,463,697 | B2 | | 11/2019 | Wardell et al. |
| 10,517,894 | B2 | | 12/2019 | Frank et al. |
| 10,533,156 | B2 | | 1/2020 | Vera et al. |
| 10,537,595 | B2 | | 1/2020 | Wardell et al. |
| 10,639,330 | B2 | | 5/2020 | Wardell et al. |
| 10,646,517 | B2 | | 5/2020 | Wardell et al. |
| 10,653,723 | B1 | | 5/2020 | Wardell et al. |
| 10,695,372 | B2 | | 6/2020 | Wardell et al. |
| 2004/0091876 | A1 | * | 5/2004 | Yabuta et al. ........... C12Q 1/68 |
| | | | | 435/6 |
| 2012/0244133 | A1 | | 9/2012 | Rosenberg et al. |
| 2013/0102075 | A1 | | 4/2013 | Vera et al. |
| 2013/0115617 | A1 | | 5/2013 | Wilson |
| 2014/0047572 | A1 | | 2/2014 | Chen et al. |
| 2014/0050708 | A1 | | 2/2014 | Powell et al. |
| 2014/0099309 | A1 | | 4/2014 | Powell et al. |
| 2016/0208216 | A1 | | 7/2016 | Vera et al. |
| 2018/0133253 | A1 | | 5/2018 | Gros et al. |

(Continued)

FOREIGN PATENT DOCUMENTS

| EP | 0446450 A1 | 9/1991 |
| EP | 3674396 A1 | 7/2020 |

(Continued)

OTHER PUBLICATIONS

Plo et al. "Genetic Alterations of the Thrombopoietin/MPL/JAK2 Axis Impacting Megakaryopoiesis" Front. Endocrinol. (Sep. 2017), 8:234, 10 pages. (Year: 2017).*

Fox et al. "F104S c-Mpl responds to a transmembrane domain-binding thrombopoietin receptor agonist: Proof of concept that selected receptor mutations in congenital amegakaryocytic thrombocytopenia can be stimulated with alternative thrombopoietic agents" Experimental Hematology 2010, 38:384-391. (Year: 2010).*

Kawahara et al. "Growth promotion of genetically modified hematopoietic progenitors using an antibody/c-Mpl chimera", Cytokine 55 (2011) 402-408. (Year: 2011).*

(Continued)

*Primary Examiner* — Christopher M Babic
*Assistant Examiner* — James Joseph Graber
(74) *Attorney, Agent, or Firm* — Alston & Bird LLP

(57) ABSTRACT

The present invention discloses cell lines and recombinant growth factor receptors useful in adoptive cell therapy (ACT), wherein the recombinant growth factor receptor can act as a molecular switch enabling cells expressing the rGFR protein to be expanded in-vitro or in- vivo. Thus the invention provides a T or NK cell, comprising a recombinant growth factor receptor (rGFR) comprising: (i) an extracellular (EC) domain; (ii) a thrombopoietin receptor transmembrane (TM) domain; and (iii) a growth factor receptor intracellular (IC) domain.

22 Claims, 8 Drawing Sheets

Figure 2:
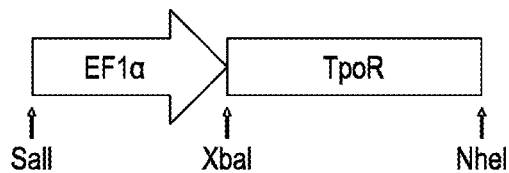

Specification includes a Sequence Listing.

(56) References Cited

U.S. PATENT DOCUMENTS

| | | |
|---|---|---|
| 2018/0282694 A1 | 10/2018 | Wardell et al. |
| 2018/0325954 A1 | 11/2018 | Wardell et al. |
| 2019/0231820 A1 | 8/2019 | Fardis |
| 2019/0276802 A1 | 9/2019 | Simpson-Abelson et al. |
| 2019/0345445 A1 | 11/2019 | Veerapathran et al. |
| 2019/0374577 A1 | 12/2019 | Ritthipichai et al. |
| 2020/0095550 A1 | 3/2020 | Vera et al. |
| 2020/0121719 A1 | 4/2020 | Lotze et al. |
| 2020/0224161 A1 | 7/2020 | Karyampudi et al. |
| 2020/0246384 A1 | 8/2020 | Wardell et al. |
| 2020/0276241 A1 | 9/2020 | Wardell et al. |
| 2020/0276242 A1 | 9/2020 | Wardell et al. |
| 2020/0277573 A1 | 9/2020 | Simpson-Abelson et al. |
| 2020/0281978 A1 | 9/2020 | Wardell et al. |
| 2020/0289569 A1 | 9/2020 | Wardell et al. |
| 2020/0299644 A1 | 9/2020 | Frank et al. |
| 2020/0306306 A1 | 10/2020 | Wardell et al. |
| 2020/0306307 A1 | 10/2020 | Wardell et al. |

FOREIGN PATENT DOCUMENTS

| | | |
|---|---|---|
| WO | 1999/023199 A1 | 5/1999 |
| WO | 2004/021995 A2 | 3/2004 |
| WO | 2011/072088 A2 | 6/2011 |
| WO | 2013/070899 A1 | 5/2013 |
| WO | 2013/173835 A1 | 11/2013 |
| WO | 2013/188427 A1 | 12/2013 |
| WO | 2014/133568 A1 | 9/2014 |
| WO | 2015/123527 A1 | 8/2015 |
| WO | 2015/131087 A1 | 9/2015 |
| WO | 2015/288839 A2 | 12/2015 |
| WO | 2017/103596 A1 | 6/2017 |
| WO | 2017/179015 A1 | 10/2017 |
| WO | 2018/081473 A1 | 5/2018 |
| WO | 2018/081789 A1 | 5/2018 |
| WO | 2018/094167 A1 | 5/2018 |
| WO | 2018/129332 A1 | 7/2018 |
| WO | 2018/129336 A1 | 7/2018 |
| WO | 2018/182817 A1 | 10/2018 |
| WO | 2018/209115 A1 | 11/2018 |
| WO | 2018/226714 A1 | 12/2018 |
| WO | 2019/100023 A1 | 5/2019 |
| WO | 2019/103857 A1 | 5/2019 |
| WO | 2019/136456 A1 | 7/2019 |
| WO | 2019/136459 A1 | 7/2019 |
| WO | 2019/160829 A1 | 8/2019 |
| WO | 2019/190579 A1 | 10/2019 |
| WO | 2019/210131 A1 | 10/2019 |
| WO | 2019/217753 A1 | 11/2019 |
| WO | 2020/061429 A1 | 3/2020 |
| WO | 2020/096682 A1 | 5/2020 |
| WO | 2020/096927 A1 | 5/2020 |
| WO | 2020/096986 A2 | 5/2020 |
| WO | 2020/096988 A2 | 5/2020 |
| WO | 2020/096989 A1 | 5/2020 |
| WO | 2020/117233 A1 | 6/2020 |
| WO | 2020/180733 A1 | 9/2020 |

OTHER PUBLICATIONS

Sogo et al. "T cell growth control using hapten-specific antibody/interleukin-2 receptor chimera", Cytokine 46 (2009) 127-136. (Year: 2009).*

Bridgeman et al. "Building Better Chimeric Antigen Receptors for Adoptive T Cell Therapy" Current Gene Therapy, 2010, 10, 77-90. (Year: 2010).*

Besser et al., 2010, Clinical Responses in a Phase II Study Using Adoptive Transfer of Short-term Cultured Tumor Infiltration Lymphocytes in Metastatic Melanoma Patients. Clinical Cancer Research 16(9):2646-55.

Donia et al., 2012, Characterization and comparison of 'standard' and 'young' tumour-infiltrating lymphocytes for adoptive cell therapy at a Danish translational research institution. Scandinavian Journal of Immunology 75(2):157-67.

Dudley, M.E. et al., 2003, Generation of Tumor-Infiltrating Lymphocyte Cultures for Use in Adoptive Transfer Therapy for Melanoma Patients, J. Immunother 26(4):332-42.

Inozume et al., 2010, Selection of CD8+PD-1+ lymphocytes in fresh human melanomas enriches for tumor-reactive T-cells. J. Immunother. 33(9):956-64.

Jin et al., 2012, Simplified method of the growth of human tumor infiltrating lymphocytes (TIL) in gas-permeable flasks to numbers needed for patient treatment. J. Immunother. 35:283.

Tran et al., 2008, Minimally Cultured Tumor-Infiltrating Lymphocytes Display Optimal Characteristics far Adoptive Cell Therapy. Journal of Immunotherapy, 31(8):742-51.

Mehrle et al., 2008, Enhancement of anti-tumor activity in vitro and in vivo by CD150 and SAP, Mol. Immunol, 45(3):796-804.

Browning et al., 2004, The T cell activation marker CD150 can be used to identify alloantigen-activated CD4+25+ regulator T cells, Cell Immunol 227(2):129-39.

Kawahara et al., 2012, Engineering of mammalian cell membrane proteins. Curr Opin Chem Engineering 1(4):411-17.

Drachman, J.G. et al., 2002, Studies with chimeric Mp1/JAK2 receptors indicate that boeh JAK2 and the membrane-proximal domain of Mp1 are required for cellular proliferation, J Biol Chem 277(26):23544-53.

Dudley, M.E. et al., 2002, Cancer regression and autoimmunity in patients after clonal repopulation with antitumor lymphocytes. Science 298(5594)850-4.

Dudley, M.E. et al., 2005, Adoptive cell transfer therapy following non-myeloablative but lymphodepleting chemotherapy for the treatment of patients with refractory metastatic melanoma. J Clin Oncol 23(10):2346-57.

Dudley, M.E. et al., 2008, Adoptive cell therapy for patients with metastatic melanoma: evaluation of intensive myeloablative chemoradiation preparative regimens. J Clin Oncol 26(32):5233-9.

Dudley, M.E. et al., 2010, CD8+ enriched "young" tumor infiltrating lymphocytes can mediate regression of metastatic melanoma. Clin Cancer Res 16(24):6122-31.

John Bridgeman, et al., Building Better Chimeric Antigen Receptors for Adoptive T Cell Therapy, Current Gene Therapy, Bentham Science Publishers Ltd, NL (Apr. 1, 2010) vol. 10, No. 2, pp. 77-90.

J. S. Bridgeman, et al., CD3[zeta]-Based Chimeric Antigen Receptors Mediate T Cell Activation via Cis- and Trans-Signalling Mechanisms: Implications for Optimization of Receptor Structure for Adoptive Cell Therapy, Clinical and Experimental Immunology (Jan. 3, 2014) vol. 175, No. 2, pp. 258-267.

Pathak Swati, et al., Eltrombopag for the Treatment of Thrombocytopenia in Patients with Malignant and Non-Malignant Hematologic Disorders, Expert Opinion on Drug Metabolism & Toxicology (Dec. 13, 2013) vol. 9, No. 12, pp. 1667-1675.

* cited by examiner

Fig. 1

Fig. 1 (continued)

SEQUENCE LISTING

```
<160> NUMBER OF SEQ ID NOS: 11

<210> SEQ ID NO 1
<211> LENGTH: 635
<212> TYPE: PRT
<213> ORGANISM: Homo sapiens
<220> FEATURE:
<221> NAME/KEY: MISC_FEATURE
<223> OTHER INFORMATION: thrombopoietin receptor

<400> SEQUENCE: 1

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
```

```
            50                  55                  60
Leu Leu Tyr Ala Tyr Pro Arg Glu Lys Pro Arg Ala Cys Pro Leu Ser
 65                  70                  75                  80

Ser Gln Ser Met Pro His Phe Gly Thr Arg Tyr Val Cys Gln Phe Pro
                 85                  90                  95

Asp Gln Glu Glu Val Arg Leu Phe Phe Pro Leu His Leu Trp Val Lys
                100                 105                 110

Asn Val Phe Leu Asn Gln Thr Arg Thr Gln Arg Val Leu Phe Val Asp
                115                 120                 125

Ser Val Gly Leu Pro Ala Pro Pro Ser Ile Ile Lys Ala Met Gly Gly
                130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
                180                 185                 190

Cys Cys Pro Ala Leu Gln Arg Pro His Ser Ala Ser Ala Leu Asp Gln
                195                 200                 205

Ser Pro Cys Ala Gln Pro Thr Met Pro Trp Gln Asp Gly Pro Lys Gln
210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
                260                 265                 270

Ser Leu Pro Val Thr Val Asp Leu Pro Gly Asp Ala Val Ala Leu Gly
                275                 280                 285

Leu Gln Cys Phe Thr Leu Asp Leu Lys Asn Val Thr Cys Gln Trp Gln
                290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
                340                 345                 350

His Phe Lys Ser Arg Asn Asp Ser Ile Ile His Ile Leu Val Glu Val
                355                 360                 365

Thr Thr Ala Pro Gly Thr Val His Ser Tyr Leu Gly Ser Pro Phe Trp
                370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
                420                 425                 430

Gln Asp Trp Lys Val Leu Glu Pro Pro Leu Gly Ala Arg Gly Gly Thr
                435                 440                 445

Leu Glu Leu Arg Pro Arg Ser Arg Tyr Arg Leu Gln Leu Arg Ala Arg
                450                 455                 460

Leu Asn Gly Pro Thr Tyr Gln Gly Pro Trp Ser Ser Trp Ser Asp Pro
465                 470                 475                 480
```

```
Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635

<210> SEQ ID NO 2
<211> LENGTH: 491
<212> TYPE: PRT
<213> ORGANISM: Homo sapiens
<220> FEATURE:
<221> NAME/KEY: MISC_FEATURE
<223> OTHER INFORMATION: Extracellular domain (EC)

<400> SEQUENCE: 2

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
            85                  90                  95

Asp Gln Glu Glu Val Arg Leu Phe Phe Pro Leu His Leu Trp Val Lys
        100                 105                 110

Asn Val Phe Leu Asn Gln Thr Arg Thr Gln Arg Val Leu Phe Val Asp
    115                 120                 125

Ser Val Gly Leu Pro Ala Pro Pro Ser Ile Ile Lys Ala Met Gly Gly
130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
            165                 170                 175

Lys Asn Ser Thr Gly Pro Thr Val Ile Gln Leu Ile Ala Thr Glu Thr
        180                 185                 190

Cys Cys Pro Ala Leu Gln Arg Pro His Ser Ala Ser Ala Leu Asp Gln
```

-continued

```
                195                 200                 205
Ser Pro Cys Ala Gln Pro Thr Met Pro Trp Gln Asp Gly Pro Lys Gln
210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
                260                 265                 270

Ser Leu Pro Val Thr Val Asp Leu Pro Gly Asp Ala Val Ala Leu Gly
                275                 280                 285

Leu Gln Cys Phe Thr Leu Asp Leu Lys Asn Val Thr Cys Gln Trp Gln
290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
                340                 345                 350

His Phe Lys Ser Arg Asn Asp Ser Ile Ile His Ile Leu Val Glu Val
                355                 360                 365

Thr Thr Ala Pro Gly Thr Val His Ser Tyr Leu Gly Ser Pro Phe Trp
370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
                420                 425                 430

Gln Asp Trp Lys Val Leu Glu Pro Pro Leu Gly Ala Arg Gly Gly Thr
                435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp
                485                 490
```

<210> SEQ ID NO 3
<211> LENGTH: 22
<212> TYPE: PRT
<213> ORGANISM: Homo sapiens
<220> FEATURE:
<221> NAME/KEY: MISC_FEATURE
<223> OTHER INFORMATION: Transmembrane domain (TM)

<400> SEQUENCE: 3

```
Ile Ser Leu Val Thr Ala Leu His Leu Val Leu Gly Leu Ser Ala Val
1               5                   10                  15

Leu Gly Leu Leu Leu Leu
            20
```

<210> SEQ ID NO 4
<211> LENGTH: 122
<212> TYPE: PRT
<213> ORGANISM: Homo sapiens
<220> FEATURE:

<221> NAME/KEY: MISC_FEATURE
<223> OTHER INFORMATION: Intracellular Domain (IC)

<400> SEQUENCE: 4

```
Arg Trp Gln Phe Pro Ala His Tyr Arg Arg Leu Arg His Ala Leu Trp
1               5                   10                  15

Pro Ser Leu Pro Asp Leu His Arg Val Leu Gly Gln Tyr Leu Arg Asp
            20                  25                  30

Thr Ala Ala Leu Ser Pro Pro Lys Ala Thr Val Ser Asp Thr Cys Glu
        35                  40                  45

Glu Val Glu Pro Ser Leu Leu Glu Ile Leu Pro Lys Ser Ser Glu Arg
    50                  55                  60

Thr Pro Leu Pro Leu Cys Ser Ser Gln Ala Gln Met Asp Tyr Arg Arg
65                  70                  75                  80

Leu Gln Pro Ser Cys Leu Gly Thr Met Pro Leu Ser Val Cys Pro Pro
                85                  90                  95

Met Ala Glu Ser Gly Ser Cys Cys Thr Thr His Ile Ala Asn His Ser
            100                 105                 110

Tyr Leu Pro Leu Ser Tyr Trp Gln Gln Pro
        115                 120
```

<210> SEQ ID NO 5
<211> LENGTH: 635
<212> TYPE: PRT
<213> ORGANISM: Homo sapiens
<220> FEATURE:
<221> NAME/KEY: MISC_FEATURE
<223> OTHER INFORMATION: TpoR F104S
<220> FEATURE:
<221> NAME/KEY: MISC_FEATURE
<222> LOCATION: (104)..()
<223> OTHER INFORMATION: F104S amino acid substitution

<400> SEQUENCE: 5

```
Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Ser Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190
```

```
Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
        245                 250                 255

Arg Ser Glu Pro Asp Gly Ile Ser Leu Gly Gly Ser Trp Gly Ser Trp
                260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
        290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
        340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
                420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
                500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
                580                 585                 590

Arg Leu Gln Pro Ser Cys Leu Gly Thr Met Pro Leu Ser Val Cys Pro
        595                 600                 605
```

```
Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635

<210> SEQ ID NO 6
<211> LENGTH: 319
<212> TYPE: PRT
<213> ORGANISM: Homo sapiens
<220> FEATURE:
<221> NAME/KEY: MISC_FEATURE
<223> OTHER INFORMATION: CD34-TpoR
<220> FEATURE:
<221> NAME/KEY: MISC_FEATURE
<222> LOCATION: (133)..(319)
<223> OTHER INFORMATION: TpoR portion

<400> SEQUENCE: 6

Met Pro Arg Gly Trp Thr Ala Leu Cys Leu Leu Ser Leu Leu Pro Ser
1               5                   10                  15

Gly Phe Met Ser Leu Asp Asn Asn Gly Thr Ala Thr Pro Glu Leu Pro
            20                  25                  30

Thr Gln Gly Thr Phe Ser Asn Val Ser Thr Asn Val Ser Tyr Gln Glu
        35                  40                  45

Thr Thr Thr Pro Ser Thr Leu Gly Ser Thr Ser Leu His Pro Val Ser
    50                  55                  60

Gln His Gly Asn Glu Ala Thr Thr Asn Ile Thr Glu Thr Thr Val Lys
65                  70                  75                  80

Phe Thr Ser Thr Ser Val Ile Thr Ser Val Tyr Gly Asn Thr Asn Ser
                85                  90                  95

Ser Val Gln Ser Gln Thr Ser Val Ile Ser Thr Val Phe Thr Thr Pro
            100                 105                 110

Ala Asn Val Ser Thr Pro Glu Thr Thr Leu Lys Pro Ser Leu Ser Pro
        115                 120                 125

Gly Asn Val Ser Leu Glu Leu Arg Pro Arg Ser Arg Tyr Arg Leu Gln
    130                 135                 140

Leu Arg Ala Arg Leu Asn Gly Pro Thr Tyr Gln Gly Pro Trp Ser Ser
145                 150                 155                 160

Trp Ser Asp Pro Thr Arg Val Glu Thr Ala Thr Glu Thr Ala Trp Ile
                165                 170                 175

Ser Leu Val Thr Ala Leu His Leu Val Leu Gly Leu Ser Ala Val Leu
            180                 185                 190

Gly Leu Leu Leu Leu Arg Trp Gln Phe Pro Ala His Tyr Arg Arg Leu
        195                 200                 205

Arg His Ala Leu Trp Pro Ser Leu Pro Asp Leu His Arg Val Leu Gly
    210                 215                 220

Gln Tyr Leu Arg Asp Thr Ala Ala Leu Ser Pro Pro Lys Ala Thr Val
225                 230                 235                 240

Ser Asp Thr Cys Glu Glu Val Glu Pro Ser Leu Leu Glu Ile Leu Pro
                245                 250                 255

Lys Ser Ser Glu Arg Thr Pro Leu Pro Leu Cys Ser Ser Gln Ala Gln
            260                 265                 270

Met Asp Tyr Arg Arg Leu Gln Pro Ser Cys Leu Gly Thr Met Pro Leu
        275                 280                 285

Ser Val Cys Pro Pro Met Ala Glu Ser Gly Ser Cys Cys Thr Thr His
    290                 295                 300

Ile Ala Asn His Ser Tyr Leu Pro Leu Ser Tyr Trp Gln Gln Pro
```

-continued

```
305              310              315

<210> SEQ ID NO 7
<211> LENGTH: 698
<212> TYPE: PRT
<213> ORGANISM: Homo sapiens
<220> FEATURE:
<221> NAME/KEY: MISC_FEATURE
<223> OTHER INFORMATION: TpoR-GCSFR
<220> FEATURE:
<221> NAME/KEY: MISC_FEATURE
<222> LOCATION: (1)..(513)
<223> OTHER INFORMATION: TpoR portion

<400> SEQUENCE: 7

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
                20                  25                  30

Ser Asp Ser Glu Pro Leu Lys Cys Phe Ser Arg Thr Phe Glu Asp Leu
            35                  40                  45

Thr Cys Phe Trp Asp Glu Glu Glu Ala Ala Pro Ser Gly Thr Tyr Gln
50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335
```

Glu Glu Lys Thr Asn Pro Gly Leu Gln Thr Pro Gln Phe Ser Arg Cys
             340                 345                 350

His Phe Lys Ser Arg Asn Asp Ser Ile Ile His Ile Leu Val Glu Val
         355                 360                 365

Thr Thr Ala Pro Gly Thr Val His Ser Tyr Leu Gly Ser Pro Phe Trp
     370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                 405                 410                 415

Ala Ala Gln Glu Thr Cys Tyr Gln Leu Arg Tyr Thr Gly Glu Gly His
             420                 425                 430

Gln Asp Trp Lys Val Leu Glu Pro Pro Leu Gly Ala Arg Gly Gly Thr
         435                 440                 445

Leu Glu Leu Arg Pro Arg Ser Arg Tyr Arg Leu Gln Leu Arg Ala Arg
     450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                 485                 490                 495

Ala Leu His Leu Val Leu Gly Leu Ser Ala Val Leu Gly Leu Leu Leu
             500                 505                 510

Leu Pro Asn Arg Lys Asn Pro Leu Trp Pro Ser Val Pro Asp Pro Ala
         515                 520                 525

His Ser Ser Leu Gly Ser Trp Val Pro Thr Ile Met Glu Glu Asp Ala
     530                 535                 540

Phe Gln Leu Pro Gly Leu Gly Thr Pro Pro Ile Thr Lys Leu Thr Val
545                 550                 555                 560

Leu Glu Glu Asp Glu Lys Lys Pro Val Pro Trp Glu Ser His Asn Ser
                 565                 570                 575

Ser Glu Thr Cys Gly Leu Pro Thr Leu Val Gln Thr Tyr Val Leu Gln
             580                 585                 590

Gly Asp Pro Arg Ala Val Ser Thr Gln Pro Gln Ser Gln Ser Gly Thr
         595                 600                 605

Ser Asp Gln Val Leu Tyr Gly Gln Leu Leu Gly Ser Pro Thr Ser Pro
     610                 615                 620

Gly Pro Gly His Tyr Leu Arg Cys Asp Ser Thr Gln Pro Leu Leu Ala
625                 630                 635                 640

Gly Leu Thr Pro Ser Pro Lys Ser Tyr Glu Asn Leu Trp Phe Gln Ala
                 645                 650                 655

Ser Pro Leu Gly Thr Leu Val Thr Pro Ala Pro Ser Gln Glu Asp Asp
             660                 665                 670

Cys Val Phe Gly Pro Leu Leu Asn Phe Pro Leu Leu Gln Gly Ile Arg
         675                 680                 685

Val His Gly Met Glu Ala Leu Gly Ser Phe
     690                 695

<210> SEQ ID NO 8
<211> LENGTH: 863
<212> TYPE: PRT
<213> ORGANISM: Homo sapiens
<220> FEATURE:
<221> NAME/KEY: MISC_FEATURE
<223> OTHER INFORMATION: TpoR-HGHR
<220> FEATURE:

<221> NAME/KEY: MISC_FEATURE
<222> LOCATION: (1)..(513)
<223> OTHER INFORMATION: TpoR portion

<400> SEQUENCE: 8

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Ala Ala Pro Ser Gly Thr Tyr Gln
50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
    370                 375                 380

Ile His Gln Ala Val Arg Leu Pro Thr Pro Asn Leu His Trp Arg Glu

```
            385                 390                 395                 400
Ile Ser Ser Gly His Leu Glu Leu Glu Trp Gln His Pro Ser Ser Trp
                    405                 410                 415

Ala Ala Gln Glu Thr Cys Tyr Gln Leu Arg Tyr Thr Gly Glu Gly His
                    420                 425                 430

Gln Asp Trp Lys Val Leu Glu Pro Leu Gly Ala Arg Gly Gly Thr
                435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
                500                 505                 510

Leu Lys Gln Gln Arg Ile Lys Met Leu Ile Leu Pro Pro Val Pro Val
                515                 520                 525

Pro Lys Ile Lys Gly Ile Asp Pro Asp Leu Leu Lys Glu Gly Lys Leu
                530                 535                 540

Glu Glu Val Asn Thr Ile Leu Ala Ile His Asp Ser Tyr Lys Pro Glu
545                 550                 555                 560

Phe His Ser Asp Asp Ser Trp Val Glu Phe Ile Glu Leu Asp Ile Asp
                565                 570                 575

Glu Pro Asp Glu Lys Thr Glu Glu Ser Asp Thr Asp Arg Leu Leu Ser
                580                 585                 590

Ser Asp His Glu Lys Ser His Ser Asn Leu Gly Val Lys Asp Gly Asp
                595                 600                 605

Ser Gly Arg Thr Ser Cys Cys Glu Pro Asp Ile Leu Glu Thr Asp Phe
                610                 615                 620

Asn Ala Asn Asp Ile His Glu Gly Thr Ser Glu Val Ala Gln Pro Gln
625                 630                 635                 640

Arg Leu Lys Gly Glu Ala Asp Leu Leu Cys Leu Asp Gln Lys Asn Gln
                645                 650                 655

Asn Asn Ser Pro Tyr His Asp Ala Cys Pro Ala Thr Gln Gln Pro Ser
                660                 665                 670

Val Ile Gln Ala Glu Lys Asn Lys Pro Gln Pro Leu Pro Thr Glu Gly
                675                 680                 685

Ala Glu Ser Thr His Gln Ala Ala His Ile Gln Leu Ser Asn Pro Ser
                690                 695                 700

Ser Leu Ser Asn Ile Asp Phe Tyr Ala Gln Val Ser Asp Ile Thr Pro
705                 710                 715                 720

Ala Gly Ser Val Val Leu Ser Pro Gly Gln Lys Asn Lys Ala Gly Met
                725                 730                 735

Ser Gln Cys Asp Met His Pro Glu Met Val Ser Leu Cys Gln Glu Asn
                740                 745                 750

Phe Leu Met Asp Asn Ala Tyr Phe Cys Glu Ala Asp Ala Lys Lys Cys
                755                 760                 765

Ile Pro Val Ala Pro His Ile Lys Val Glu Ser His Ile Gln Pro Ser
                770                 775                 780

Leu Asn Gln Glu Asp Ile Tyr Ile Thr Thr Glu Ser Leu Thr Thr Ala
785                 790                 795                 800

Ala Gly Arg Pro Gly Thr Gly Glu His Val Pro Gly Ser Glu Met Pro
                805                 810                 815
```

Val Pro Asp Tyr Thr Ser Ile His Ile Val Gln Ser Pro Gln Gly Leu
            820                 825                 830

Ile Leu Asn Ala Thr Ala Leu Pro Leu Pro Asp Lys Glu Phe Leu Ser
            835                 840                 845

Ser Cys Gly Tyr Val Ser Thr Asp Gln Leu Asn Lys Ile Met Pro
    850                 855                 860

<210> SEQ ID NO 9
<211> LENGTH: 877
<212> TYPE: PRT
<213> ORGANISM: Homo sapiens
<220> FEATURE:
<221> NAME/KEY: MISC_FEATURE
<223> OTHER INFORMATION: TpoR-PrlR
<220> FEATURE:
<221> NAME/KEY: MISC_FEATURE
<222> LOCATION: (1)..(513)
<223> OTHER INFORMATION: TpoR portion

<400> SEQUENCE: 9

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

-continued

```
Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Lys Gly Tyr Ser Met Val Thr Cys Ile Phe Pro Pro Val Pro Gly
        515                 520                 525

Pro Lys Ile Lys Gly Phe Asp Ala His Leu Leu Glu Lys Gly Lys Ser
530                 535                 540

Glu Glu Leu Leu Ser Ala Leu Gly Cys Gln Asp Phe Pro Pro Thr Ser
545                 550                 555                 560

Asp Tyr Glu Asp Leu Leu Val Glu Tyr Leu Glu Val Asp Asp Ser Glu
                565                 570                 575

Asp Gln His Leu Met Ser Val His Ser Lys Glu His Pro Ser Gln Gly
            580                 585                 590

Met Lys Pro Thr Tyr Leu Asp Pro Asp Thr Asp Ser Gly Arg Gly Ser
        595                 600                 605

Cys Asp Ser Pro Ser Leu Leu Ser Glu Lys Cys Glu Glu Pro Gln Ala
610                 615                 620

Asn Pro Ser Thr Phe Tyr Asp Pro Glu Val Ile Glu Lys Pro Glu Asn
625                 630                 635                 640

Pro Glu Thr Thr His Thr Trp Asp Pro Gln Cys Ile Ser Met Glu Gly
                645                 650                 655

Lys Ile Pro Tyr Phe His Ala Gly Gly Ser Lys Cys Ser Thr Trp Pro
            660                 665                 670

Leu Pro Gln Pro Ser Gln His Asn Pro Arg Ser Ser Tyr His Asn Ile
        675                 680                 685

Thr Asp Val Cys Glu Leu Ala Val Gly Pro Ala Gly Ala Pro Ala Thr
690                 695                 700

Leu Leu Asn Glu Ala Gly Lys Asp Ala Leu Lys Ser Ser Gln Thr Ile
```

```
                705                 710                 715                 720
Lys Ser Arg Glu Glu Gly Lys Ala Thr Gln Gln Arg Glu Val Glu Ser
                    725                 730                 735

Phe His Ser Glu Thr Asp Gln Asp Thr Pro Trp Leu Leu Pro Gln Glu
                    740                 745                 750

Lys Thr Pro Phe Gly Ser Ala Lys Pro Leu Asp Tyr Val Glu Ile His
                    755                 760                 765

Lys Val Asn Lys Asp Gly Ala Leu Ser Leu Leu Pro Lys Gln Arg Glu
                    770                 775                 780

Asn Ser Gly Lys Pro Lys Pro Gly Thr Pro Glu Asn Asn Lys Glu
785                 790                 795                 800

Tyr Ala Lys Val Ser Gly Val Met Asp Asn Asn Ile Leu Val Leu Val
                    805                 810                 815

Pro Asp Pro His Ala Lys Asn Val Ala Cys Phe Glu Glu Ser Ala Lys
                    820                 825                 830

Glu Ala Pro Pro Ser Leu Glu Gln Asn Gln Ala Glu Lys Ala Leu Ala
                    835                 840                 845

Asn Phe Thr Ala Thr Ser Ser Lys Cys Arg Leu Gln Leu Gly Gly Leu
                    850                 855                 860

Asp Tyr Leu Asp Pro Ala Cys Phe Thr His Ser Phe His
865                 870                 875

<210> SEQ ID NO 10
<211> LENGTH: 799
<212> TYPE: PRT
<213> ORGANISM: Homo sapiens
<220> FEATURE:
<221> NAME/KEY: MISC_FEATURE
<223> OTHER INFORMATION: TpoR-IL2R?
<220> FEATURE:
<221> NAME/KEY: MISC_FEATURE
<222> LOCATION: (1)..(513)
<223> OTHER INFORMATION: TpoR portion

<400> SEQUENCE: 10

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
                    20                  25                  30

Ser Asp Ser Glu Pro Leu Lys Cys Phe Ser Arg Thr Phe Glu Asp Leu
                35                  40                  45

Thr Cys Phe Trp Asp Glu Glu Glu Ala Ala Pro Ser Gly Thr Tyr Gln
            50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                    85                  90                  95

Asp Gln Glu Glu Val Arg Leu Phe Phe Pro Leu His Leu Trp Val Lys
                100                 105                 110

Asn Val Phe Leu Asn Gln Thr Arg Thr Gln Arg Val Leu Phe Val Asp
            115                 120                 125

Ser Val Gly Leu Pro Ala Pro Pro Ser Ile Ile Lys Ala Met Gly Gly
        130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175
```

-continued

```
Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
    370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
            485                 490                 495

Ala Leu His Leu Val Leu Gly Leu Ser Ala Val Leu Gly Leu Leu Leu
        500                 505                 510

Leu Asn Cys Arg Asn Thr Gly Pro Trp Leu Lys Lys Val Leu Lys Cys
    515                 520                 525

Asn Thr Pro Asp Pro Ser Lys Phe Phe Ser Gln Leu Ser Ser Glu His
    530                 535                 540

Gly Gly Asp Val Gln Lys Trp Leu Ser Ser Pro Phe Pro Ser Ser Ser
545                 550                 555                 560

Phe Ser Pro Gly Gly Leu Ala Pro Glu Ile Ser Pro Leu Glu Val Leu
                565                 570                 575

Glu Arg Asp Lys Val Thr Gln Leu Leu Leu Gln Gln Asp Lys Val Pro
            580                 585                 590
```

```
Glu Pro Ala Ser Leu Ser Ser Asn His Ser Leu Thr Ser Cys Phe Thr
            595                 600                 605

Asn Gln Gly Tyr Phe Phe Phe His Leu Pro Asp Ala Leu Glu Ile Glu
        610                 615                 620

Ala Cys Gln Val Tyr Phe Thr Tyr Asp Pro Tyr Ser Glu Glu Asp Pro
625                 630                 635                 640

Asp Glu Gly Val Ala Gly Ala Pro Thr Gly Ser Ser Pro Gln Pro Leu
                645                 650                 655

Gln Pro Leu Ser Gly Glu Asp Asp Ala Tyr Cys Thr Phe Pro Ser Arg
                660                 665                 670

Asp Asp Leu Leu Leu Phe Ser Pro Ser Leu Leu Gly Gly Pro Ser Pro
            675                 680                 685

Pro Ser Thr Ala Pro Gly Gly Ser Gly Ala Gly Glu Glu Arg Met Pro
            690                 695                 700

Pro Ser Leu Gln Glu Arg Val Pro Arg Asp Trp Asp Pro Gln Pro Leu
705                 710                 715                 720

Gly Pro Pro Thr Pro Gly Val Pro Asp Leu Val Asp Phe Gln Pro Pro
                725                 730                 735

Pro Glu Leu Val Leu Arg Glu Ala Gly Glu Glu Val Pro Asp Ala Gly
                740                 745                 750

Pro Arg Glu Gly Val Ser Phe Pro Trp Ser Arg Pro Pro Gly Gln Gly
            755                 760                 765

Glu Phe Arg Ala Leu Asn Ala Arg Leu Pro Leu Asn Thr Asp Ala Tyr
            770                 775                 780

Leu Ser Leu Gln Glu Leu Gln Gly Gln Asp Pro Thr His Leu Val
785                 790                 795

<210> SEQ ID NO 11
<211> LENGTH: 1905
<212> TYPE: DNA
<213> ORGANISM: Artificial Sequence
<220> FEATURE:
<223> OTHER INFORMATION: Codon optimised human sequence
<220> FEATURE:
<221> NAME/KEY: MISC_FEATURE
<223> OTHER INFORMATION: Codon optimised sequence based on human TpoR
      sequence

<400> SEQUENCE: 11
atgccctcct gggccctctt catggtcacc tcctgcctcc tcctggcccc tcaaaacctg      60
gcccaagtca gcagccaaga tgtctccttg ctggcatcag actcagagcc cctgaagtgt     120
ttctcccgaa catttgagga cctcacttgc ttctgggatg aggaagaggc agcgcccagt     180
gggacatacc agctgctgta tgcctacccg cgggagaagc ccgtgcttg ccccctgagt      240 tcccagagca tgcccacttt ggaacccga tacgtgtgcc agtttccaga ccaggaggaa      300
gtgcgtctct tctttccgct gcacctctgg gtgaagaatg tgttcctaaa ccagactcgg     360
actcagcgag tcctctttgt ggacagtgta ggcctgccgg ctccccccag tatcatcaag     420
gccatgggtg ggagccagcc aggggaactt cagatcagct gggaggagcc agctccagaa     480
atcagtgatt tcctgaggta cgaactccgc tatggcccca gagatcccaa gaactcccact    540 ggtcccacgg tcatacagct gattgccaca gaaacctgct gccctgctct gcagaggcct    600
cactcagcct ctgctctgga ccagtctcca tgtgctcagc cacaatgcc ctggcaagat      660 ggaccaaagc agacctcccc aagtagagaa gcttcagctc tgacagcaga gggtggaagc     720
tgcctcatct caggactcca gcctggcaac tcctactggc tgcagctgcg cagcgaacct    780
```

-continued

```
gatgggatct ccctcggtgg ctcctgggga tcctggtccc tccctgtgac tgtggacctg    840
cctggagatg cagtggcact tggactgcaa tgctttacct tggacctgaa gaatgttacc    900
tgtcaatggc agcaacagga ccatgctagc tcccaaggct tcttctacca cagcagggca    960
cggtgctgcc ccagagacag gtacccatc tgggagaact gcgaagagga agagaaaaca   1020
aatccaggac tacagacccc acagttctct cgctgccact tcaagtcacg aaatgacagc   1080
attattcaca tccttgtgga ggtgaccaca gccccgggta ctgttcacag ctacctgggc   1140
tcccctttct ggatccacca ggctgtgcgc ctccccaccc caaacttgca ctggagggag   1200
atctccagtg ggcatctgga attggagtgg cagcacccat cgtcctgggc agcccaagag   1260
acctgttatc aactccgata cacaggagaa ggccatcagg actggaaggt gctggagccg   1320
cctctcgggg cccgaggagg gaccctggag ctgcgcccgc gatctcgcta ccgtttacag   1380
ctgcgcgcca ggctcaacgg ccccacctac caaggtccct ggagctcgtg gtcggaccca   1440
actagggtgg agaccgccac cgagaccgcc tggatctcct tggtgaccgc tctgcatcta   1500
gtgctgggcc tcagcgccgt cctgggcctg ctgctgctga ggtggcagtt tcctgcacac   1560
tacaggagac tgaggcatgc cctgtggccc tcacttccag acctgcaccg ggtcctaggc   1620 cagtaccta gggacactgc agccctgagc ccgcccaagg ccacagtctc agatacctgt   1680
gaagaagtgg aacccagcct ccttgaaatc ctccccaagt cctcagagag gactcctttg   1740
cccctgtgtt cctcccaggc ccagatggac taccgaagat tgcagccttc ttgcctgggg   1800
accatgcccc tgtctgtgtg cccacccatg gctgagtcag ggtcctgctg taccacccac   1860
attgccaacc attcctacct accactaagc tattggcagc agcct                   1905
```

CELLS EXPRESSING RECOMBINANT GROWTH FACTOR RECEPTORS

RELATED APPLICATION

This application is a national stage filing under 35 U.S.C. § 371 of International Patent Application Serial No. PCT/GB2016/053949, filed Dec. 15, 2016, the entire contents of which is incorporated herein by reference in its entirety.

FIELD OF THE INVENTION

The present invention relates to a cell comprising a recombinant growth factor receptor (rGFR) useful in adoptive cell therapy (ACT). The recombinant growth factor receptor can act as a molecular switch enabling cells expressing the rGFR protein to be expanded in-vitro or in-vivo. The present invention also provides rGFR proteins, nucleic acid encoding the rGFRs, and therapeutic uses thereof.

BACKGROUND TO THE INVENTION

Adoptive cell therapy (ACT) using autologous T-cells to mediate cancer regression has shown much promise in early clinical trials. Several general approaches have been taken such as the use of naturally occurring tumour reactive or tumour infiltrating lymphocytes (TILs) expanded ex vivo. Additionally, T-cells may be modified genetically to retarget them towards defined tumour antigens. This can be done via the gene transfer of peptide (p)-major histocompatibility complex (MHC) specific T-cell Receptors (TCRs) or synthetic fusions between tumour specific single chain antibody fragment (scFv) and T-cell signalling domains (e.g. CD3ζ), the latter being termed chimeric antigen receptors (CARs). TIL and TCR transfer has proven particularly good when targeting Melanoma (Rosenberg et al. 2011; Morgan 2006), whereas CAR therapy has shown much promise in the treatment of certain B-cell malignancies (Grupp et al. 2013).

The current general treatment protocol for ACT requires an initial non-myeloablative preconditioning treatment using cyclophosphamide and/or fludarabine which removes most of the circulating lymphocytes in the patients prior to reinfusion of the ex vivo grown cells. This allows space for the new cells to expand and removes potential 'cytokine sinks' by which normal cells compete with the newly infused cells for growth and survival signals. Along with the cells patients receive cytokine support via infusions of high doses of interleukin(IL)-2 which helps the new cells engraft and expand.

There are a number of factors which currently limit the technology of T-cell ACT. Current preconditioning therapy described above requires hospital admission and potentially leaves patients in an immunocompromised state. Furthermore, many patients are not in a healthy enough state to be able to withstand the rigours of this treatment regimen. Beyond preconditioning the use of IL-2 as a supportive therapy is associated with severe toxicity and potential intensive care treatment. Indeed, TIL therapy itself, unlike TCR and CAR therapy, has not been associated with any serious on or off target toxicities, with the majority of toxicity events being associated with the accompanying IL-2 infusions.

Methods by which preconditioning and IL-2 supportive treatments can be minimised or reduced will have major benefits in that they will: (i) reduce patient hospitalisation, (ii) increase the proportion of potential patients who could be treated by ACT, (iii) reduce the clinical costs associated with extensive hospital admission, thus again opening up the possibility of ACT to more patients.

Thus there is a need for new ACT therapies that minimise the need for preconditioning treatments and/or IL-2 supportive treatments.

The present invention uses cells that express a recombinant growth factor receptor which can be turned on or off by the administration of a ligand for the rGFR, which may be a clinically validated drug. This permits expansion of target cells in-vivo with minimal toxicity to other cells.

A number of reports have used the idea of growth factor receptor engineering as a means of expanding certain populations of cells or for the development of selection processes for antibody engineering strategies. For example, a number of reports have demonstrated that antibody-TpoR or EpoR fusions could be used to for a number of biotechnology strategies such as single chain antibody selections (Ueda et al. 2000, Kawahara et. Al. 2004), and a number of reports have demonstrated that growth factor receptor fusions can successfully expand the megakaryocyte cell line Ba/F3 and/or haematopoietic stem cells (Jin et al. 2000; Richard et al. 2000; Nagashima et al. 2003; Kawahara et al 2011; Saka et al. 2013).

The thrombopoietin (Tpo) receptor (TpoR; CD110, c-mpl) is normally expressed in cells of the megakaryocyte lineage. In its normal state the TpoR is switched on in response to thrombopoietin, which causes megakaryocyte production of platelets. There is also an active negative feedback loop by which platelet expression of TpoR can be used as a sink to reduce circulating levels of Tpo. Importantly TpoR is not expressed on any other normal tissue or cancer cells (Columbyova 1995).

However, there have been no reports of T-cells, or other lymphocytes, being engineered to express rGFRs, such as TpoR or a mutant thereof, and no reports of the use of these cells in ACT.

FIGURES

Figure 1:
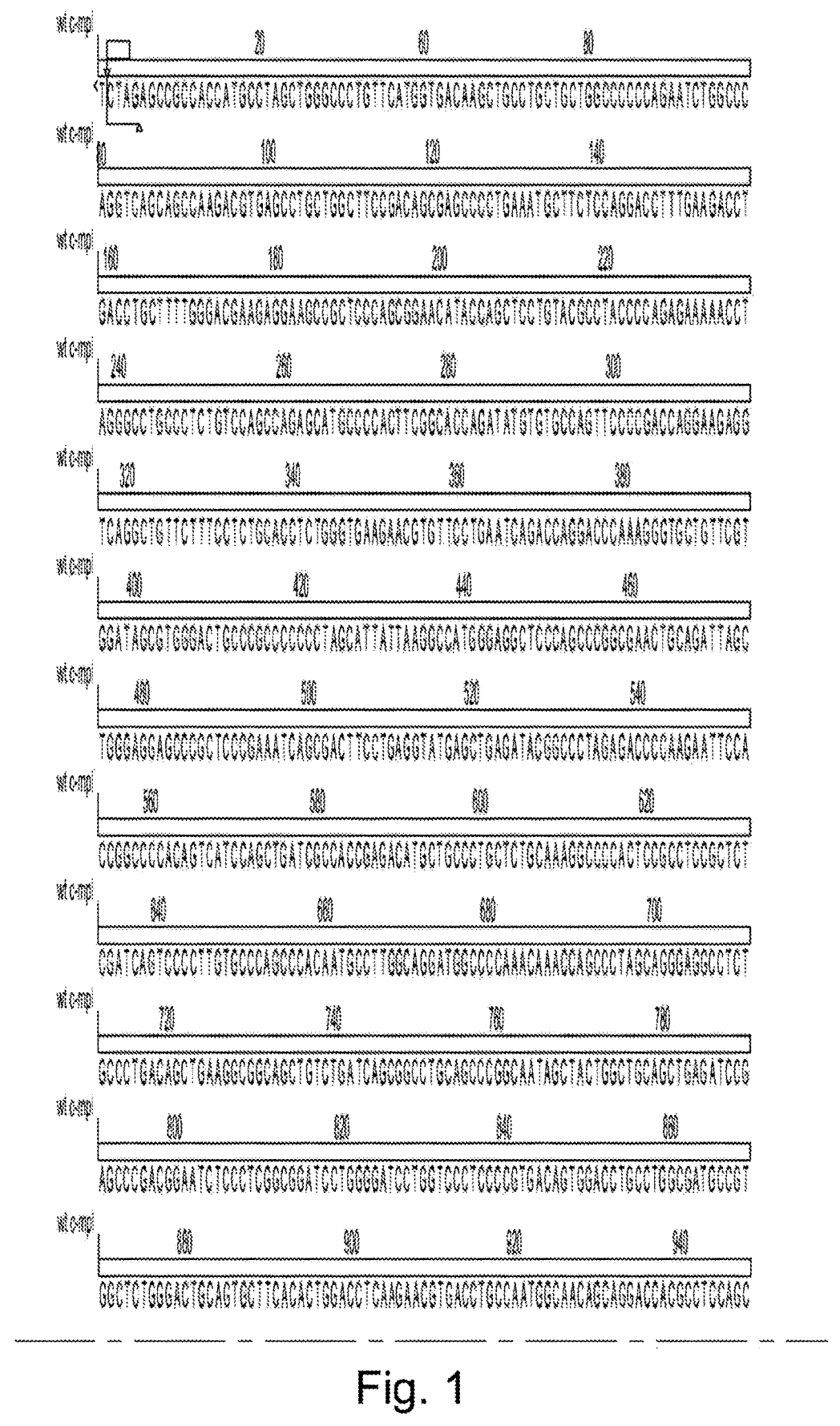
Figure 1:
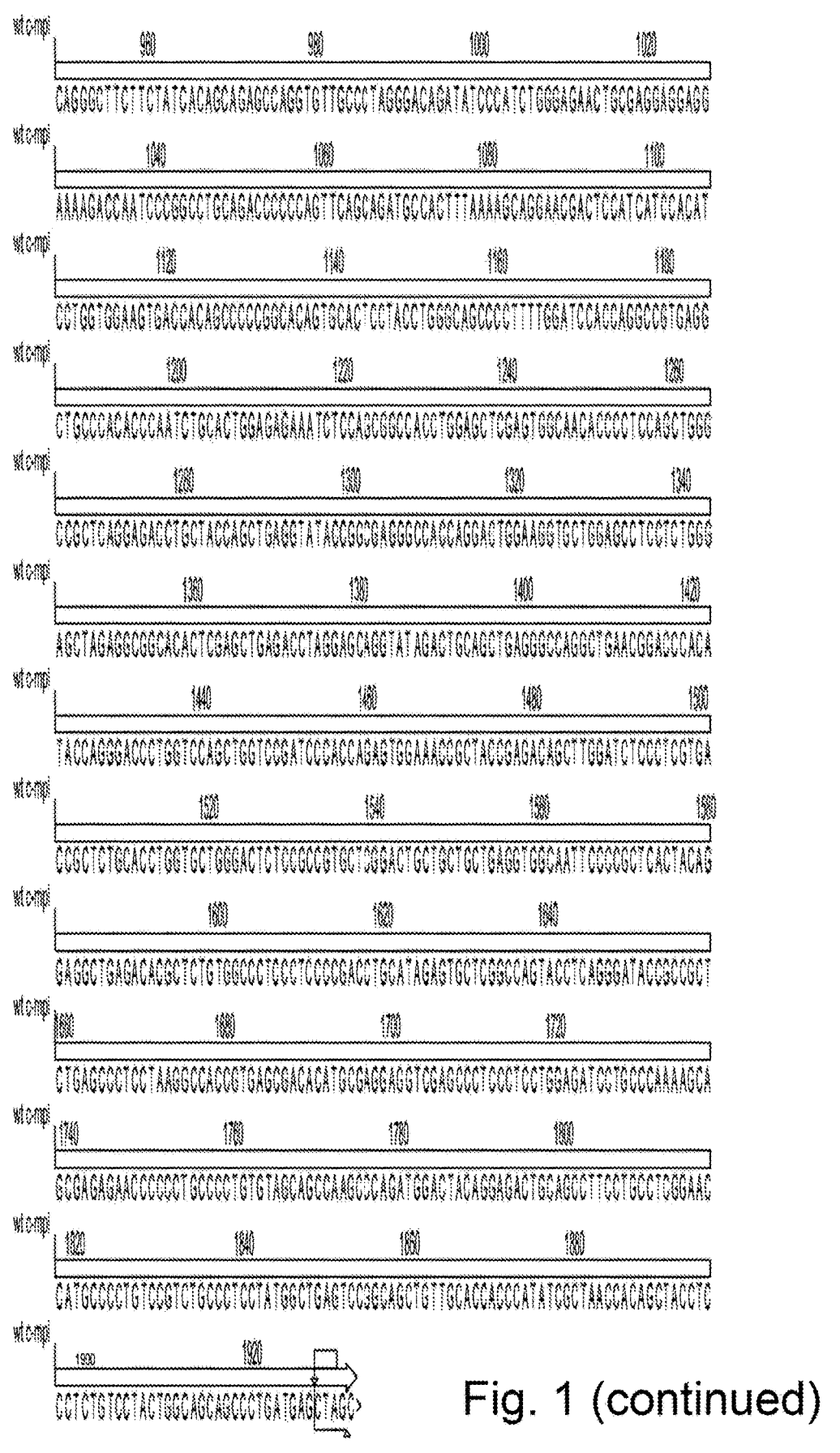

FIG. 1—Codon optimized sequence of c-mpl (TopR) (SEQ ID NO:11). Sequence shows the entire open reading frame of the c-mpl (TpoR).

FIG. 2—Schematic representation of the gene organisation of the lentiviral transgene. The TpoR transgene was codon optimised and cloned downstream of the EF1α promoter by way of an Xbal and Nhel restriction digest pair in the pSF.Lenti Lentiviral vector.

Figure 3:
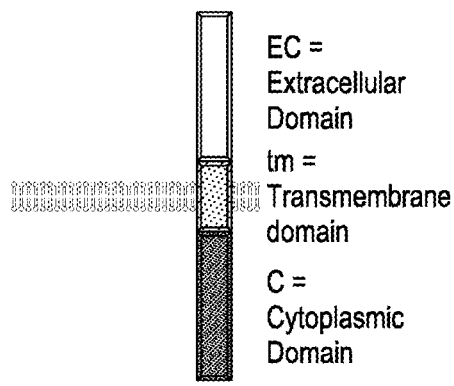

FIG. 3—Schematic representation of modular T-cell growth signal receptor. EC consists of an extracellular domain which may be derived from a native growth factor receptor, a single chain antibody or selectable marker such as CD34. Tm comprises a transmembrane sequence which anchors the polypeptide to the cell surface membrane. The Tm sequence would be derived from the human thrombopoietin receptor. C consists of a cytoplasmic domain derived from a wild type or mutated growth factor receptor.

Figure 4:
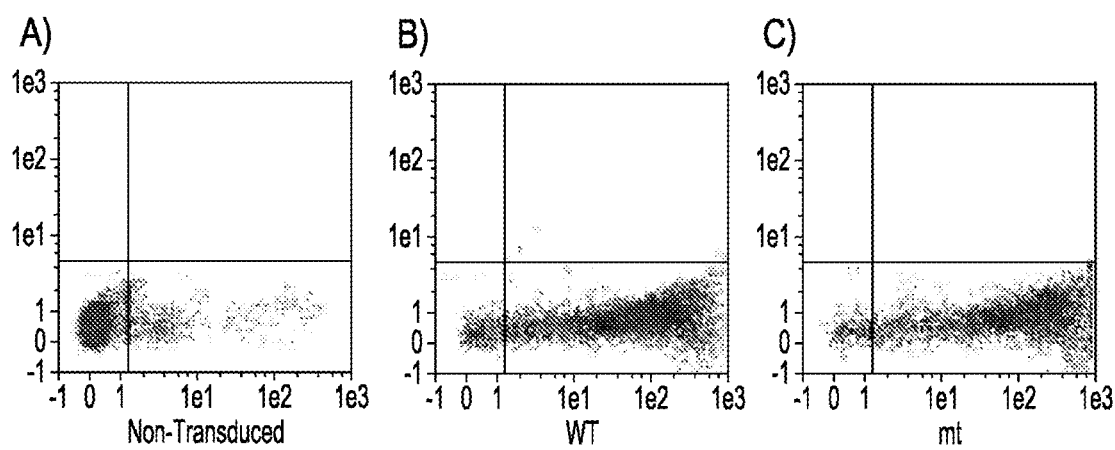

FIG. 4—Flow analysis of non-transduced, wildtype (WT) and mutant truncated (mt) TpoR expression in primary human T-cells. Primary human T-cells were transduced with lentiviral particles carrying the indicated transgenes. Expression was assessed 72 h post infection using anti-CD110-PE antibodies.

Figure 5:
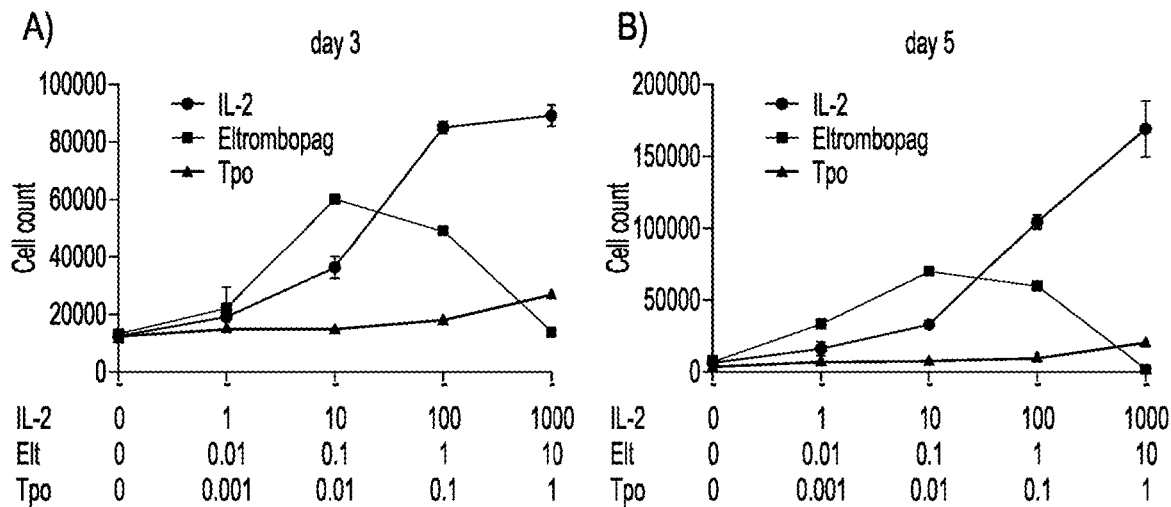

FIG. 5—Analysis of responsiveness of modular T-cell growth signal receptor engineered T-cells to varying concentrations of IL-2, Eltrombopag (Elt) or thrombopoietin (Tpo). Transduced primary human T-cells were incubated with the indicated concentrations of each drug and cells counted after three and five days FIG. 6—Enrichment kinetics of modular T-cell growth signal receptor engineered T-cells to varying concentrations of IL-2, Eltrombopag (Elt) or thrombopoietin (Tpo). Transduced primary human T-cells were diluted with non-transduced cells to a 20% transduction level. Cells were incubated with the indicated concentrations of each drug and the enrichment of each population established at the indicated time points by staining cells with anti-CD110-PE antibodies.

Figure 7:
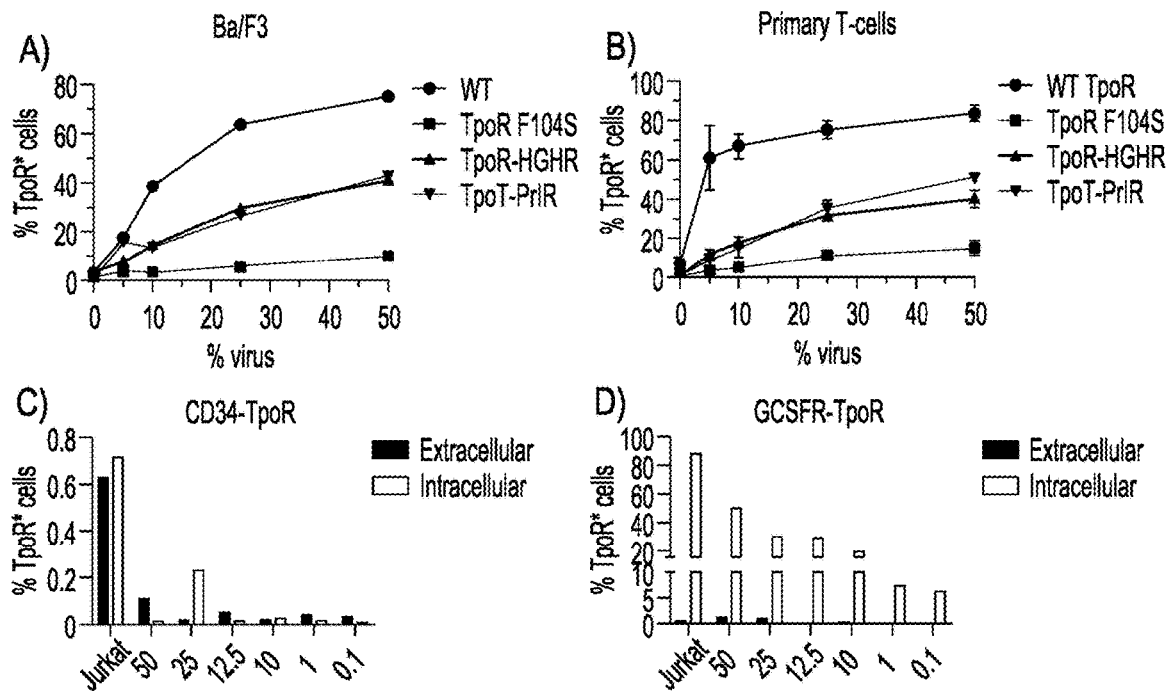

FIG. 7—Titration of lentiviral supernatants carrying genes for rGFR variants. Lentiviral supernatants were generated by transient transfection of 293T cells. Supernatants were added to Ba/F3 cells (A) and primary human T-cells (B) at the indicated concentrations. CD34-TpoR fusion (C) and TpoR-GCSFR (D) viral titration is shown extracellular and intracellular on Jurkat and primary human T-cells.

Figure 8:
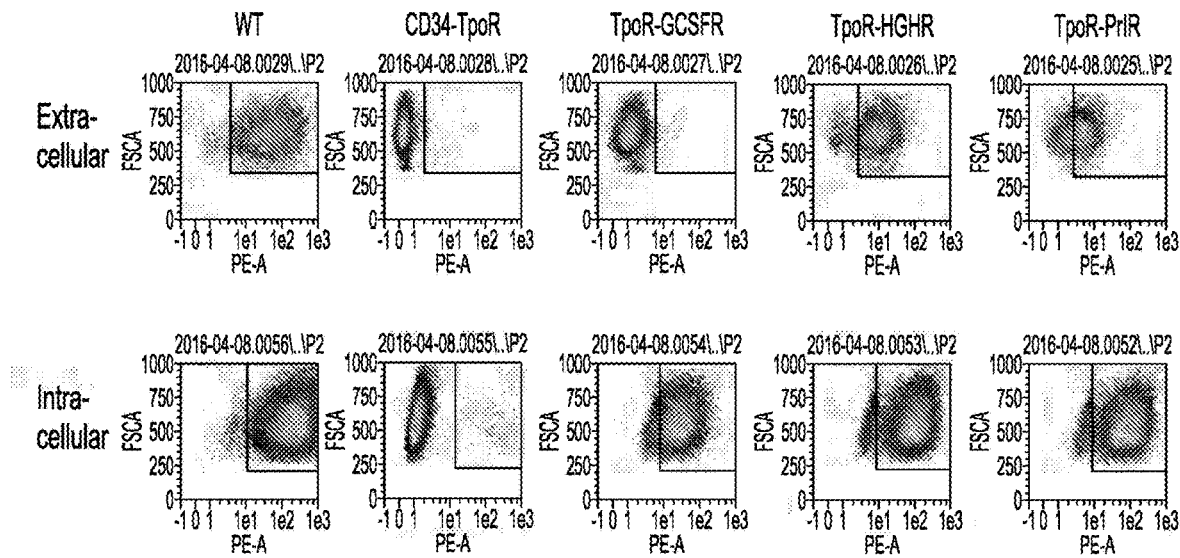

FIG. 8—Flow cytometry plots of rGFR in Jurkat T-cells. Lentiviral supernatants carrying genes for the indicated rGFR variants were added to Jurkat T-cells and expression determined after 3 days using PE conjugated anti-CD110 or anti-CD34 antibodies.

Intracellular staining was performed using BD Cell Fixation/Permeabilisation Kit. Cells were analysed on a MACSQuant® analyser.

Figure 9:
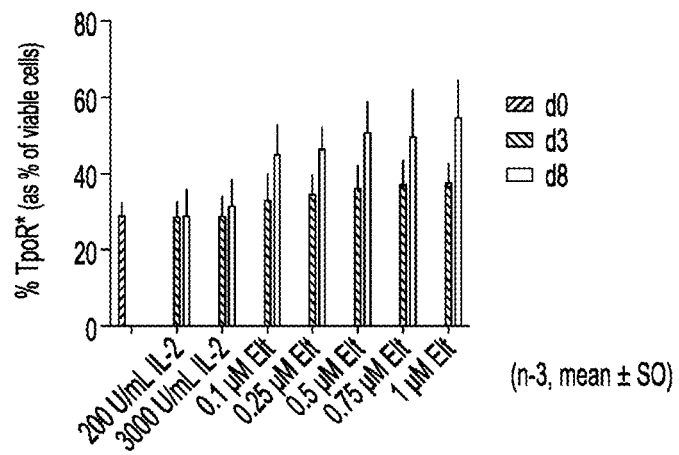

FIG. 9—Titration of Eltrombopag on primary human T-cells. Primary human T-cells from three donors were transduced with the WT TpoR and incubated in the presence of IL2 or Eltrombopag at the indicated concentrations. At day 3 and 8 cells were removed and the proportion of cells expressing the receptor assessed using PE conjugated anti-CD110 antibodies and a MACSQuant® analyser.

Figure 10:
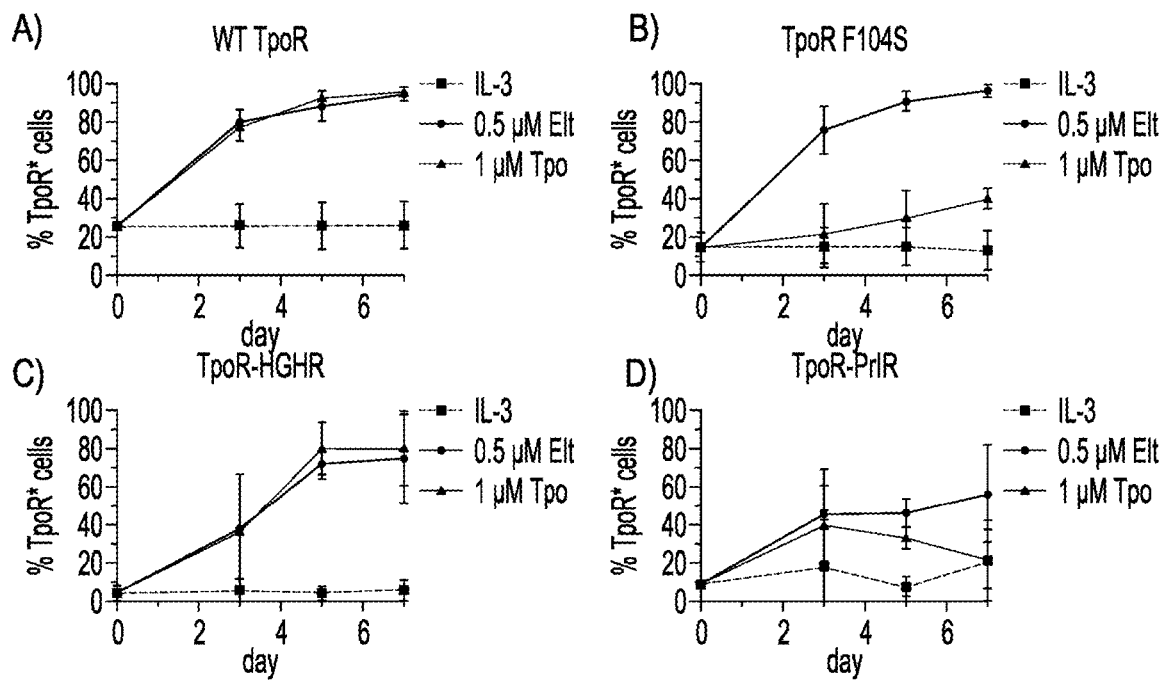

FIG. 10—Analysis of rGFR variants in Ba/F3 cells. The IL3 dependent cell line Ba/F3 was transduced with the indicated rGFR variants and incubated in the presence of 1 .mu.M Tpo, 0.5 .mu.M Eltrombopag or 0.5 ng/ml IL3. Cells were taken at days 3, 5 and 7 stained with PE conjugated anti-CD110 antibodies and analysed using a MACSQuant® analyser.

Figure 11:
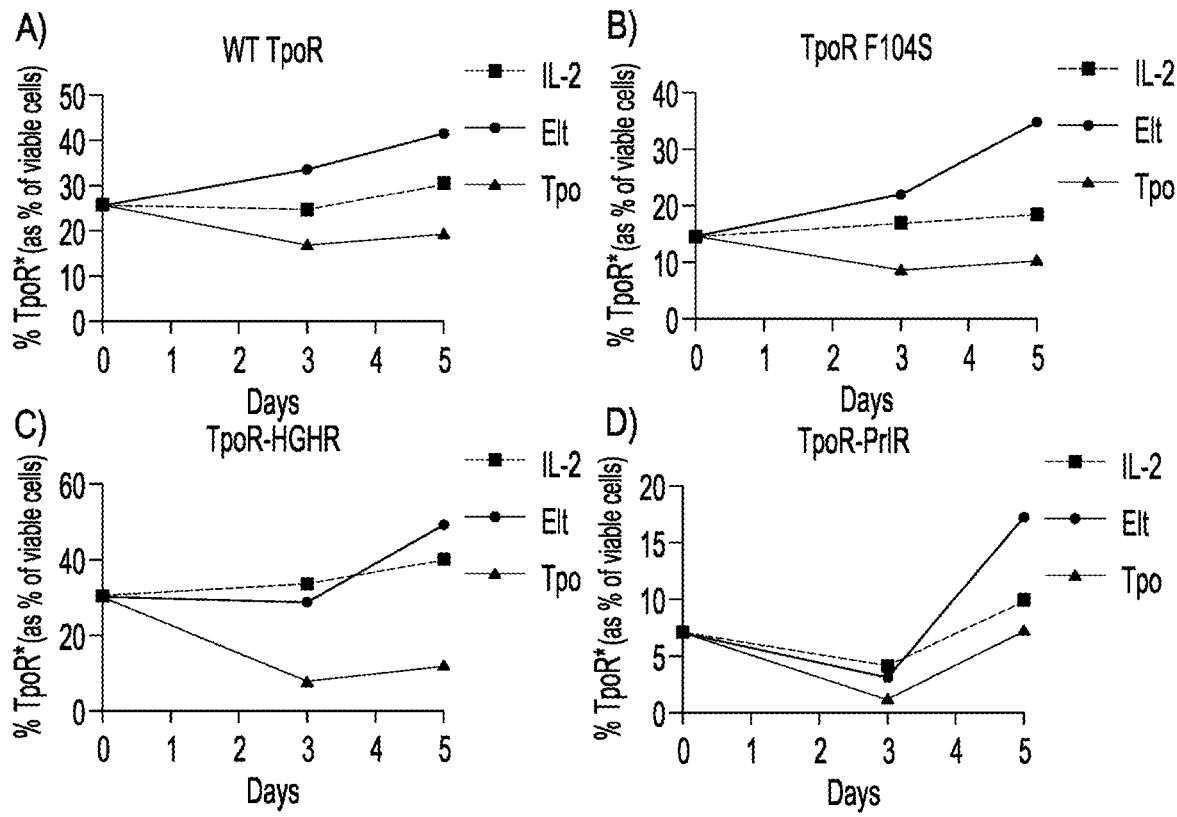

FIG. 11—Analysis of rGFR variants in primary human T-cells cells. Primary human T-cells from a healthy donor were transduced with the indicated rGFR variants and incubated in the presence of 1 .mu.M Tpo, 0.5 .mu.M Eltrombopag or 0.5 ng/ml IL3. Cells were taken at days 3 and 5 stained with PE conjugated anti-CD110 antibodies and analysed using a MACSQuant® analyser.

Figure 12:
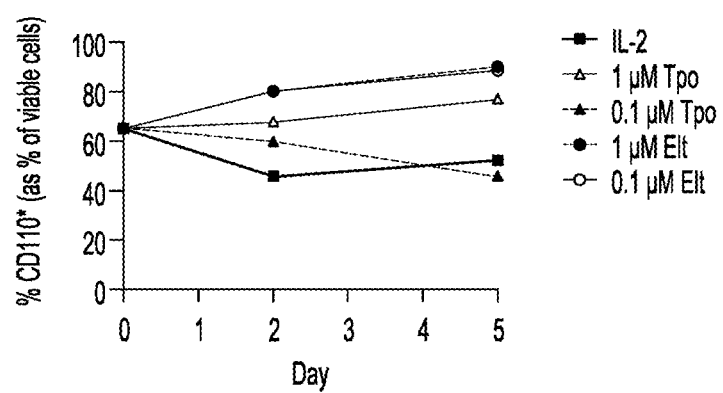

FIG. 12—Analysis of WT TpoR activity in Melanoma Tumour Infiltrating Lymphocytes. Tumour infiltrating lymphocytes (TIL) established from a cutaneous melanoma lesion were lentivirally transduced with the WT TpoR rGFR. The TIL were incubated in the presence of 200 IU/ml IL2 or the indicated concentrations of Tpo or Eltrombopag. At days 2 and 5 cells were removed, stained with PE conjugated anti-CD110 antibodies and analysed using a MACSQuant® analyser.

Figure 13:
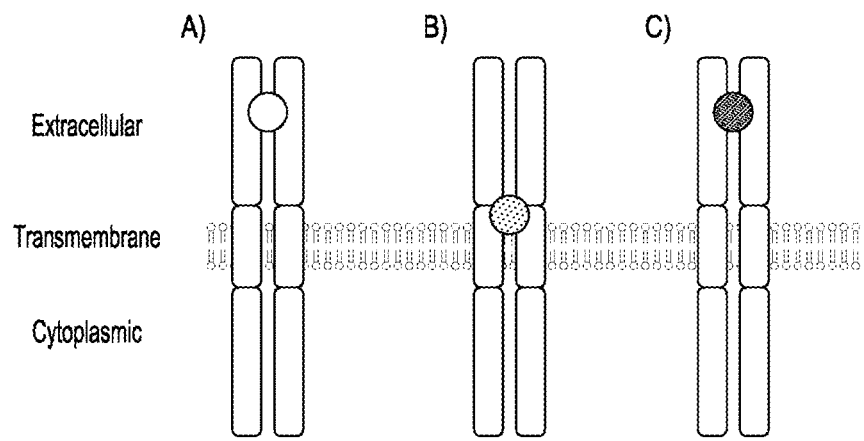

FIG. 13—is a schematic diagram showing a number of possible rGFR configurations.

(A) the native EC domain (such as TpoR EC domain) which binds growth factors (red) could be used to activate the receptor, (B) a drug which binds the TM domain (light grey) could be used, in which case the EC domain is redundant. The EC domain could then take the form of a marker gene such as truncated CD34 for selection and/or in vivo monitoring.

(C) the EC domain could be replaced with a receptor which allows controlled dimerization upon addition of a dimerising agent (Dark grey)

Figure 14:
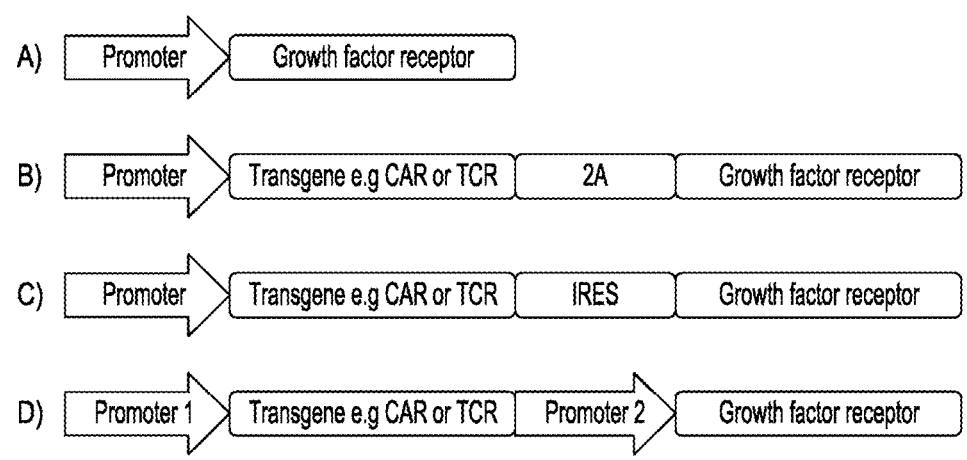

FIG. 14 is a schematic diagram showing a number of possible configurations of the nucleic acid constructs of the present invention.

A. The growth factor receptor may be expressed alone under the control of a promoter in a therapeutics population of cells, for example Tumour Infiltrating Lymphocytes B. The growth factor receptor may be expressed along with a therapeutics transgene such as a Chimeric Antigen Receptor (CAR) or T-cell Receptor (TCR) with the therapeutic transgene and growth factor receptor separated by a self cleaving polypeptide linker such as 2A C. The growth factor receptor may be expressed along with a therapeutics transgene such as a Chimeric Antigen Receptor (CAR) or T-cell Receptor (TCR) with the therapeutic transgene and growth factor receptor separated by an internal ribosome entry sequence (IRES)

D. The growth factor receptor may be expressed along with a therapeutic transgene such as a Chimeric Antigen Receptor (CAR) or T-cell Receptor (TCR).

Note: The position of the growth factor may be upstream (5') or downstream (3') of the therapeutic transgene when expressed from the same promoter. The therapeutic transgene and growth factor receptors may be under the control of separate promoters either on the same or different plasmids.

SUMMARY OF ASPECTS OF THE INVENTION

The present inventors have shown that it is possible to engineer lymphocytes, including T cells and NK cells that comprise a rGFR that can function as a growth switch. This allows the lymphocytes to be expanded in-vivo by administering the rGFR ligand to the patient. The inventors have shown that an rGFR, for example, based on the thrombopoietin (Tpo) receptor (TpoR; CD110, c-mpl), induces proliferation of the engineered lymphocyte following binding of an rGFR ligand to the receptor. Thus the ligand causes proliferation of cells that express the rGFR but is expected to have low toxicity due to the absence, or low expression, of receptors on other cells in the patient. rGFRs based on TpoR or other related growth factor receptors would be a valuable tool to augment lymphocyte expansion in vitro and in vivo for adoptive cell therapies.

Thus in a first aspect, the present invention provides a lymphocyte, including a T cell or NK cell, comprising a recombinant growth factor receptor (rGFR) comprising:

(i) an extracellular (EC) domain;
(ii) a thrombopoietin transmembrane (TM) domain; and
(iii) a growth factor receptor intracellular (IC) domain.

The rGFR is designed such that binding of the receptor ligand to the rGFR results in receptor activation and growth signalling to the cell to induce proliferation and/or survival. The rGFR may comprise the TM domain shown in SEQ ID No: 3 (also referred to herein as TpoR or human c-mpl TM domain) or a derivative or variant thereof that maintains signalling and cell proliferation in response to ligand binding.

The ligand may be human thrombopoietin, a thrombopoietin receptor agonist, e.g. Eltrombopag, or a tumour associated antigen.

The EC domain may be the human c-mpl EC domain (as shown in SEQ ID No: 2), which binds to human Tpo) or may be one or more of i) a truncated EC domain, ii) a truncated c-mpl EC domain, iii) a domain that binds to a tumour associated antigen, iv) an antibody or antibody fragment that binds to a tumour associated antigen; and v) a selection marker, for example CD34.

The IC domain of the rGFR may include a JAK binding domain. The IC domain may be from human growth hormone receptor, human prolactin receptor or the human thrombopoietin receptor (c-mpl).

The lymphocyte may be a T cell, including a Tumour Infiltrating Lymphocyte (TIL) a T Regulatory Cell (Treg) or a primary T cell, or an NK cell, or a dendritic cell.

In addition to the rGFR the lymphocyte, T or NK cell, may include a recombinant T-cell receptor (TCR) or Chimeric Antigen Receptor (CAR).

In a second aspect the invention provides a nucleic acid sequence encoding the rGFR.

In a third aspect the invention provides a vector which comprises a nucleic acid sequence according to the second aspect and, if present, a TCR and/or CAR nucleic acid sequence.

In a fourth aspect the invention provides a method for making a lymphocyte, or T or NK cell, according to the first aspect of the invention, which comprises the step of introducing a nucleic acid encoding the rGFR, or vector, into the lymphocyte.

In a fifth aspect the invention provides a pharmaceutical composition which comprises a vector according to the third aspect, or lymphocyte (including a T or NK cell) according to the first aspect, together with a pharmaceutically acceptable carrier, diluent or excipient.

In a sixth aspect the invention provides a method of in-vivo cell expansion comprising administering the lymphocytes, or T or NK cells, of the first aspect, or pharmaceutical composition of the fifth aspect to a subject. The cells may be expanded in-vivo by administering thrombopoietin, or a thrombopoietin agonist such as Eltrombopag, to a subject. Optionally, the cells may be expanded ex-vivo using a thrombopoietin, or a thrombopoietin agonist such as Eltrombopag prior to administration to the subject.

In a seventh aspect the invention provides a lymphocyte, including a T or NK cell, according to the first aspect, or vector according to the third aspect, for use in adoptive cell therapy.

In an eighth aspect the invention provides a lymphocyte, including a T or NK cell, according to the first aspect, or vector according to the third aspect, for use in a method of treating cancer.

In a ninth aspect the invention provides the use of a lymphocyte according to the first aspect, or the use of the vector according to the third aspect in the manufacture of a medicament for treating cancer.

In a tenth aspect the invention provides Eltrombopag or Tpo for use in adoptive cell therapy.

In an eleventh aspect the invention provides Eltrombopag or Tpo for use in the in-vivo or ex-vivo expansion of lymphocytes, including T or NK cells.

In a twelfth aspect the invention provides a lymphocyte, including T or NK cells, of the first aspect for use in combination with thrombopoietin or a thrombopoietin receptor agonist, for example Eltrombopag, in the treatment of a cancer.

In a further aspect there is provided a cell comprising a rGFR having an amino acid sequence with at least 80, 85, 90 or 95% identity to the amino acid sequence set out in SEQ ID No: 1, 5, 6, 7, 8, 9 or 10.

DETAILED DESCRIPTION

Recombinant Growth Factor Receptor (rGFR)

Provided herein are recombinant growth factor receptors (rGFR) comprising: (i) an extracellular (EC) domain; (ii) a thrombopoietin transmembrane (TM) domain; and (iii) a growth factor receptor intracellular (IC) domain. In a simple form the rGFR may be the full length of the human Tpo receptor (a codon optimised nucleic acid sequence of which is provided in FIG. 1 and SEQ ID No:11 herein and amino acid sequence in SEQ ID NO:1) or derivative or variant thereof that maintains signalling and cell proliferation, or cell survival, in response to ligand binding. The rGFR may be of modular form with the EC, TM and IC domains derived from different receptors. However, the rGFR must maintain its ability to transmit a growth signal to the cell upon ligand binding. The rGFR may be activated and transmit a growth signal to the cell upon ligand binding to the TM domain.

Suitable rGFRs may be selected based on GFRs with limited expression on normal human tissue, for example, GFRs that are expressed on only a small cell population or confined to a specific cell type, for example, c-kit. Alternatively, the native ligand binding domain of the growth factor receptor may be removed and e.g. replaced with a marker or other EC domain.

In some embodiments the rGFR comprises an EC domain comprising a ligand, such as an antibody or antibody fragment that binds to a tumour associated antigen, and a TM and IC domain from TpoR (c-mpl).

The rGFR may comprise an EC domain without growth factor binding function (for example a truncated form of the TpoR EC domain) and/or a marker, for example CD34), and the TM and IC domains from TpoR. Growth of cells carrying this type of receptor may then be stimulated by Eltrombopag binding to the TM domain.

There are a number of cytokine receptors with structural similarity to TpoR which could be used to generate novel chimeric GFRs. For example, the granulocyte colony stimulating factor receptor (GCSFR), human growth hormone receptor (HGHR) and prolactin receptor (PrlR) are all single chain and homodimeric making them ideal candidates for lentiviral gene transfer and subsequent T-cell surface expression.

The rGFR may comprise a TpoR EC and a TpoR TM domains with an IC domain from GCSFR, HGHR or PrlR.

In other embodiments, the rGFR may comprise a TpoR IC domain and a TpoR TM domain with an EC domain from CD34 (referred to herein as CD34-TpoR and shown in SEQ ID NO: 6). The CD34 EC domain may replace all, or a portion of, the TpoR EC domain.

In another embodiment, the rGFR is a TpoR containing an extracellular point mutation, F104S, for example, as shown in SEQ ID NO: 5, which has been shown to prevent responsiveness to Thrombopoietin but not Eltrombopag (Fox et al 2010).

The rGFR may be expressed alone under the control of a promoter in a therapeutic population of cells that have therapeutic activity, for example, Tumour Infiltrating Lymphocytes (TILs).

Alternatively, the GFR may be expressed along with a therapeutic transgene such as a Chimeric Antigen Receptor (CAR) and/or T-cell Receptor (TCR), for example as described in FIG. 14. Suitable TCRs and CARs are well known in the literature, for example HLA-A*02-NYESO-1 specific TCRs (Rapoport et al. Nat Med 2015) or anti-CD19scFv.CD3 fusion CARs (Kochenderfer et al. J Clin Oncol 2015) which have been successfully used to treat Myeloma or B-cell malignancies respectively. The rGFRs described herein may be expressed with any known CAR or TCR thus providing the cell with a regulatable growth switch to allow cell expansion in-vitro or in-vivo, and a conventional activation mechanism in the form of the TCR or CAR for anti-cancer activity. Thus the invention provides a cell for use in adoptive cell therapy comprising a rGFR as described herein and a TCR and/or CAR that specifically binds to a tumour associated antigen.

The rGFR may have the sequence shown as SEQ ID No: 1 or a variant thereof. The rGFR may have the TM domain (SEQ ID No: 3) and IC domain (SEQ ID No: 4) of the human Tpo receptor and a truncated Tpo receptor EC domain (without native ligand binding function).

The rGFR may have the sequence shown as SEQ ID No: 5, which is the human TpoR sequence having a F104S amino acid substitution. Amino acids The rGFR may have the sequence shown as SEQ ID No: 6 (also referred to herein as CD34-TpoR) or a variant thereof. As shown in SEQ ID No:6, amino acids 1 to 132 are the CD34 portion and amino acids 133 to 319 are from TpoR.

The rGFR may have the sequence shown as SEQ ID No: 7, which comprises the TpoR EC and TM domains with a GCSFR IC domain. For example, as shown in SEQ ID No: 7, amino acids 1 to 513 are the TpoR portion with amino acids 514-698 from GCSFR.

The rGFR may have the sequence shown as SEQ ID No: 8, (also referred to herein as TpoR-HGHR) or a variant thereof. As shown in SEQ ID No: 8, amino acids 1 to 513 are the TpoR portion with an EC domain (amino acids 514-863) from HGHR.

The rGFR may have the sequence shown as SEQ ID No: 9, (also referred to herein as TpoR-PrIR) or a variant thereof. As shown in SEQ ID No: 9, amino acids 1 to 513 are the TpoR portion with an EC domain (amino acids 514-877) from PrIR.

The rGFR may have the sequence shown as SEQ ID No: 10, (also referred to herein as TpoR-IL2RB) or a variant thereof. As shown in SEQ ID No: 10, amino acids 1 to 513 are the TpoR portion with an EC domain (amino acids 514-799) from IL2RB.

In embodiments there is provided a cell comprising an rGFR having at least 80, 85, 90 or 95% identity to the amino acid sequence set out in SEQ ID No: 1, 5,6,7,8, 9 or 10

As will be apparent to the skilled person, the rGFRs as described herein are generally intended for expression in human cells, thus, typically, are constructed based on human sequences.

As will be apparent to the skilled person the rGFRs and cells comprising the rGFRS the described herein may be useful in any of the methods as described herein.

EC Domain

The EC domain may be the EC domain from TpoR (SEQ ID No: 2) or derivative or variant thereof that maintains signalling and cell proliferation, or in response to ligand binding to the receptor.

The EC domain may be a native EC domain which binds growth factors that could be used to activate the receptor.

The EC domain may not be required for rGFR signalling for example if TM domain is used that can cause receptor activation upon ligand binding e.g. the TpoR TM domain. The EC domain may then be a truncated native domain (e.g. without ligand binding function). For example, a truncated TpoR EC domain. The native EC domain may be replaced by a marker such as truncated CD34 for selection and/or in vivo monitoring.

The EC domain may be the TpoR EC domain having a F104S mutation. This mutation has been shown to prevent responsiveness to Thrombopoietin but not Eltrombopag (Fox et al 2010).

The EC domain may be replaced with a receptor which allows controlled dimerization upon addition of a dimerising agent, for example an EC domain comprising FKBP with rapamycin as a dimerising agent.

The EC domain may be different to the TM and IC domain. The EC domain may bind other ligands and could be antibody like allowing the growth factor receptor signalling domain to respond to a defined antigen. In this case a ligand binding- EC domain may be used to activate the receptor when it binds to its cognate molecule.

The EC domain may comprise an amino acid sequence from CD34, for example, as shown in SEQ ID No: 6.

TM Domain

The TM domain from the Tpo receptor (TpoR) as shown in SEQ ID No: 3 may be used, including a derivative or variant thereof that maintains signalling and cell proliferation or survival in response to ligand binding to the receptor. In some embodiments the TM domain may have at least 80, 85, 90 or 95% identity to the amino acid sequence set out in SEQ ID No: 3. This may be useful because TpoR is known to have limited expression in normal human tissues and it is also known to bind to Eltrombopag, thus an rGFR comprising a TM domain from the Tpo receptor can a be activated by exposing the cells in-vitro or in-vivo to a clinically validated compound with a known toxicity profile.

IC Domain

The growth factor receptor intracellular (IC) domain (shown in FIG. 1 and SEQ ID No: 4) from the Tpo receptor may be used including a derivative or variant thereof that maintains signalling and cell proliferation in response to ligand binding to the receptor. This may be combined with the TM domain from the Tpo receptor to achieve good levels of cell proliferation in response to ligand binding.

Other IC domains that are growth factor receptor like may be suitable for use in constructing the rGFRs of the present invention, as these receptors are known to activate the same cell signalling pathways as the Tpo receptor. For example, the IC domains from G-CSF, GM-CSF, prolactin, human growth hormone or IL2RB (see, for example, the IC domains of the rGFRs in SEQ ID No: 7,8,9 or 10) may be used to construct rGFRs when combined with the TpoR TM domain. The ability of an rGFR comprising these IC domains to induce cell proliferation or survival in response to a receptor agonist, for example, Eltrombopag, may then be determined using the methods described in the Examples herein.

Cells

The cells used in the present invention may be any lymphocyte that is useful in adoptive cell therapy, such as a T-cell or a natural killer (NK) cell, an NKT cell, a gamma/delta T-cell or T regulatory cell. The cells may be allogenic or autologous.

T cells or T lymphocytes are a type of lymphocyte that have a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Cytolytic T cells (TC cells, or CTLs) destroy virally infected cells and tumor cells, and are also implicated in transplant rejection. CTLs express the CD8 molecule at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEM RA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+Treg cells have been described—naturally occurring Treg cells and adaptive Treg cells.

Naturally occurring Treg cells (also known as CD4+CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner.

NK cells (belonging to the group of innate lymphoid cells) are defined as large granular lymphocytes (LGL) and constitute the third kind of cells differentiated from the common lymphoid progenitor generating B and T lymphocytes.

Tumour-infiltrating lymphocytes are white blood cells that have left the bloodstream and migrated into a tumour. They are mononuclear immune cells, a mix of different types of cells (i.e., T cells, B cells, NK cells, macrophages) in variable proportions, T cells being the most abundant cells. They can often be found in the stroma and within the tumour itself.

TILs are implicated in killing tumor cells. The presence of lymphocytes in tumours is often associated with better clinical outcomes.

Nucleic Acids

An aspect of the invention provides a nucleic acid sequence of the invention, encoding any of the rGFRs, polypeptides, or proteins described herein (including functional portions and functional variants thereof).

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed ,e.g. codon optimisation.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid sequence may encode the protein sequence shown as SEQ ID No. 1 or a variant thereof, including a nucleic acid sequence encoding a truncated form of the Tpo receptor which has lacks the last five amino acids of the wild type Tpo receptor and thus has a truncated IC domain.

The nucleotide sequence may comprise the codon optimised human TpoR nucleic acid sequence shown in FIG. 1 or variants thereof.

The invention also provides a nucleic acid sequence which comprises a nucleic acid sequence encoding a rGFR and a further nucleic acid sequence encoding a T-cell receptor (TCR) and/or chimeric antigen receptor (CAR).

The nucleic acid sequences may be joined by a sequence allowing co-expression of the two or more nucleic acid sequences. For example, the construct may comprise an internal promoter, an internal ribosome entry sequence (IRES) sequence or a sequence encoding a cleavage site. The cleavage site may be self-cleaving, such that when the polypeptide is produced, it is immediately cleaved into the discrete proteins without the need for any external cleavage activity.

Various self-cleaving sites are known, including the Foot-and-Mouth disease virus (FMDV) and the 2a self-cleaving peptide.

The co-expressing sequence may be an internal ribosome entry sequence (IRES). The co-expressing sequence may be an internal promoter.

Vectors

In an aspect, the present invention provides a vector which comprises a nucleic acid sequence or nucleic acid construct of the invention.

Such a vector may be used to introduce the nucleic acid sequence(s) or nucleic acid construct(s) into a host cell so that it expresses one or more rGFR(s) according to the first aspect of the invention and, optionally, one or more other proteins of interest (POI), for example a TCR or a CAR.

The vector may, for example, be a plasmid or a viral vector, such as a retroviral vector or a lentiviral vector, or a transposon based vector or synthetic mRNA. Vectors derived from retroviruses, such as the lentivirus, are suitable tools to achieve long-term gene transfer since they allow long-term, stable integration of a transgene or transgenes and its propagation in daughter cells.

The vector may be capable of transfecting or transducing a lymphocyte including a T cell or an NK cell.

The present invention also provides vectors in which a nucleic acid of the present invention is inserted.

The expression of natural or synthetic nucleic acids encoding a rGFR, and optionally a TCR or CAR is typically achieved by operably linking a nucleic acid encoding the rGFR and TCR/CAR polypeptide or portions thereof to one or more promoters, and incorporating the construct into an expression vector. The vectors can be suitable for replication and integration in eukaryotic cells. Typical cloning vectors contain transcription and translation terminators, initiation sequences, and promoters useful for regulation of the expression of the desired nucleic acid sequence.

Viral vector technology is well known in the art and is described, for example, in Sambrook et al. (2001, Molecular Cloning: A Laboratory Manual, Cold Spring Harbor Laboratory, New York), and in other virology and molecular biology manuals, see also, WO 01/96584; WO 01/29058; and U.S. Pat. No. 6,326,193).

In some embodiments, the nucleic acid constructs are as shown in FIG. 14. In some embodiments the nucleic acids are multicystronic constructs that permit the expression of multiple transgenes (e.g., rGFR and a TCR and/or CAR etc.) under the control of a single promoter. In some embodiments, the transgenes (e.g., rGFR and a TCR and/or CAR etc.) are separated by a self-cleaving 2A peptide. Examples of 2A peptides useful in the nucleic acid constructs of the invention include F2A, P2A, T2A and E2A. In other embodiments of the invention, the nucleic acid construct of the invention is a multicystronic construct comprising two promoters; one promoter driving the expression of rGFR and the other promoter driving the expression of the TCR or CAR. In some embodiments, the dual promoter constructs of the invention are uni-directional. In other embodiments, the dual promoter constructs of the invention are bi-directional.

In order to assess the expression of the rGFR polypeptide or portions thereof, the expression vector to be introduced into a cell can also contain either a selectable marker gene or a reporter gene or both to facilitate identification and selection of expressing cells from the population of cells sought to be transfected or transduced through viral vectors. The rGFR polypeptide may incorporate a marker, such as CD34, as part of the EC domain.

Pharmaceutical Composition

The present invention also relates to a pharmaceutical composition containing a vector or a rGFR expressing cell of the invention together with a pharmaceutically acceptable carrier, diluent or excipient, and optionally one or more further pharmaceutically active polypeptides and/or compounds. Such a formulation may, for example, be in a form suitable for intravenous infusion.

Method Of Treatment

Cells, including T and NK cells, expressing rGFRs for use in the methods of the present may either be created ex vivo either from a patient's own peripheral blood (autologous), or in the setting of a haematopoietic stem cell transplant from donor peripheral blood (allogenic), or peripheral blood from an unconnected donor (allogenic). The cells may be tumour infiltrating lymphocytes (TILs). Alternatively, T-cells or NK cells may be derived from ex-vivo differentiation of inducible progenitor cells or embryonic progenitor cells to T-cells or NK cells. In these instances, T-cells expressing a rGFR and, optionally, a CAR and/or TCR, are generated by introducing DNA or RNA coding for the rGFR and, optionally, a CAR and/or TCR, by one of many means including transduction with a viral vector, transfection with DNA or RNA.

T or NK cells expressing a rGFR of the present invention and, optionally, expressing a TCR and/or CAR may be used for the treatment of haemotological cancers or solid tumours.

A method for the treatment of disease relates to the therapeutic use of a vector or cell, including a T or NK cell, of the invention. In this respect, the vector, or T or NK cell may be administered to a subject having an existing disease or condition in order to lessen, reduce or improve at least one symptom associated with the disease and/or to slow down, reduce or block the progression of the disease. The method of the invention may cause or promote T-cell mediated killing of cancer cells.

The vector, or T or NK cell according to the present invention may be administered to a patient with one or more additional therapeutic agents. The one or more additional therapeutic agents can be coadministered to the patient. By "coadministering" is meant administering one or more additional therapeutic agents and the vector, or T or NK cell of the present invention sufficiently close in time such that the vector, or T or NK cell can enhance the effect of one or more additional therapeutic agents, or vice versa. In this regard, the vectors or cells can be administered first and the one or more additional therapeutic agents can be administered second, or vice versa. Alternatively, the vectors or cells and the one or more additional therapeutic agents can be administered simultaneously. Suitable therapeutic agents that may be co-administered with the vectors or cells of the present invention include any growth factor receptor agonist that activates the rGFR, for example, Eltrombopag (rINN, codenamed SB-497115-GR) or Romiplostim .

Eltrombopag may be particularly useful in the methods of the invention as its toxicity profile is known. In preclinical studies, the compound was shown to interact selectively with the thrombopoietin receptor, leading to activation of the JAK-STAT signalling pathway and increased proliferation and differentiation of megakaryocytes. Animal studies confirmed that administration could increase platelet counts. In 73 healthy volunteers, higher doses of Eltrombopag caused larger increases in the number of circulating platelets without tolerability problems, see, for example, Jenkins JM, Williams D, Deng Y, Uhl J, Kitchen V, Collins D, Erickson-Miller CL (June 2007). "Phase 1 clinical study of eltrombopag, an oral, nonpeptide thrombopoietin receptor agonist". Blood 109 (11): 4739-41. Thus in the methods of the invention suitable dosages of Eltrombopag may be determined based on previously published clinical studies and the in-vitro assays described herein.

Another agent that may be useful is IL-2, as this is currently used in existing cell therapies to boost the activity of administered cells. However, as stated earlier, IL-2 treatment is associated with toxicity and tolerability issues. Thus it is an aim of present invention to stimulate cell proliferation using an agonist that binds to the rGFR and, therefore, reduce the amount of IL-2 that must be administered (e.g. to levels that are less toxic) or even eliminate the need for IL-2 administration.

For purposes of the inventive methods, wherein cells are administered to the patient, the cells can be cells that are allogeneic or autologous to the patient.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above and tables described below.

EXAMPLES

Example 1—Production of T-cells expressing rGFR

Materials and Methods

Construct design—The entire human TpoR nucleic acid sequence, or mutant truncated variant lacking the final five N-terminal amino acids and described in Saka et al. 2013 The constructs were cloned into pSF.Lenti (Oxford Genetics) via an XbaI and NheI site. The CD34 fusion receptor was generated by fusing the extracellular domain of CD34 directly to the transmembrane and cytoplasmic domain of the human TpoR. The HGHR, PrlR and GCSFR fusions were generated by fusing the HGHR, PrlR or GCSFR cytoplasmic domains respectively directly to the extracellular and transmembrane domain of the TpoR. The F104S mutant was generated by cloning in a fragment of the TpoR via XbaI and XhoI restriction sites. All fragments and constructs were codon optimised and gene synthesised by Genewiz.

Lentiviral Production—Lentiviral production was performed using a three-plasmid packaging system (Cell Biolabs, San Diego, USA) by mixing 10 µg of each plasmid, plus 10 µg of the pSF.Lenti lentiviral plasmid containing the transgene, together in serum free RPMI containing 50 mM CaCl2. The mixture was added dropwise to a 50% confluent monolayer of 293T cells in 75 cm2 flasks. The viral supernatants were collected at 48 and 72h post transfection, pooled and concentrated using LentiPac lentiviral supernatant concentration (GeneCopoeia, Rockville, Md., USA) solution according to the manufacturer's instructions. Lentiviral supernatants were concentrated 10-fold and used to directly infect primary human T-cells in the presence of 4 pg/ml polybrene (Sigma-Aldrich, Dorset, UK).

Peripheral blood mononuclear cells were isolated from normal healthy donors before activation for 24 hours with T-cell activation and expansion beads (Invitrogen) according to the manufacturer's instructions before addition of lentiviral supernatants.

Following expansion cells were washed excessively to remove any exogenous IL2 and plated into 96-well U-bottom plates. Cells were supplemented with IL2 (Proleukin), recombinant human Tpo (Miltenyi Biotec) or Eltrombopag (Stratech Scientific, Suffolk, UK). At various time points thereafter cells were either stained with a 1:400 dilution of eFlor-450 fixable viability dye (eBioscience, UK) and counted directly from the wells using a MACSQuant Cytometer, or were stained with viability dye plus phycoerythrin conjugated anti-CD110 antibodies (Miltenyi Biotec, UK) and analysed using a MACSQuant cytomter. Cell viability and/or transduction level was then analysed using MACSQuantify software (Miltenyi Biotec, UK).

RESULTS—Primary human T-cells were isolated from Buffy coats obtained from the NHSBT. T-cells were isolated by Ficoll-mediated isolation. The isolated T-cells were activated with human T-cell activation and expansion beads. Cells were incubated with concentrated lentiviral particles and expanded over a number of days. The lentivirus contained the DNA sequence of full length human TpoR or a truncated variant thereof lacking the final five aa which has previously been demonstrated to enhance the growth responsiveness of haematopoietic stem cells to Tpo (Saka et al. 2013), under the control of an EF1a promoter (FIGS. 1 & 2). Following expansion transduction levels were assessed by directly staining for the TpoR protein using anti-CD110 antibodies. FIG. 4 shows transduction efficiency of VVT and mt TpoR variants in primary human T-cells compared with non-transduced cells. Transduction efficiencies of >90% could be achieved whereas non-transduced cells were 5% positive for TpoR.

Initially VVT transduced cells with a transduction level of 94% were plated at $5 \times 10^4$ cells/well in 96-well U-bottom plates and incubated with varying concentrations of IL-2, Eltrombopag or Tpo. After three and five days the cells were stained with EFlor-450 Live/dead fixable viability dye and the cells in each well counted by flow cytometry. FIG. 5 demonstrates dose dependent responses in relative increase of cell number as the concentration of each compound increases. It appears however that responses to Eltrombopag are maximal at around 0.1 µM with concentrations above this becoming toxic. We did not see maximal responses to Tpo comparable to those seen with Eltrombopag or IL-2, possibly as optimal concentrations were not used.

Additional cells were diluted with non-transduced cells to achieve a population with 20% transduction efficiency. The T-cells were incubated with 100 IU/ml IL-2; 0.1, 0.5 or 1.0 pg/ml Eltrombopag; or 1.0 or 10.0 µg/ml recombinant human Tpo. After three, six and nine days the cells were stained with anti-CD110 (TpoR) antibodies and analysed by flow cytometry.

Figure 6:
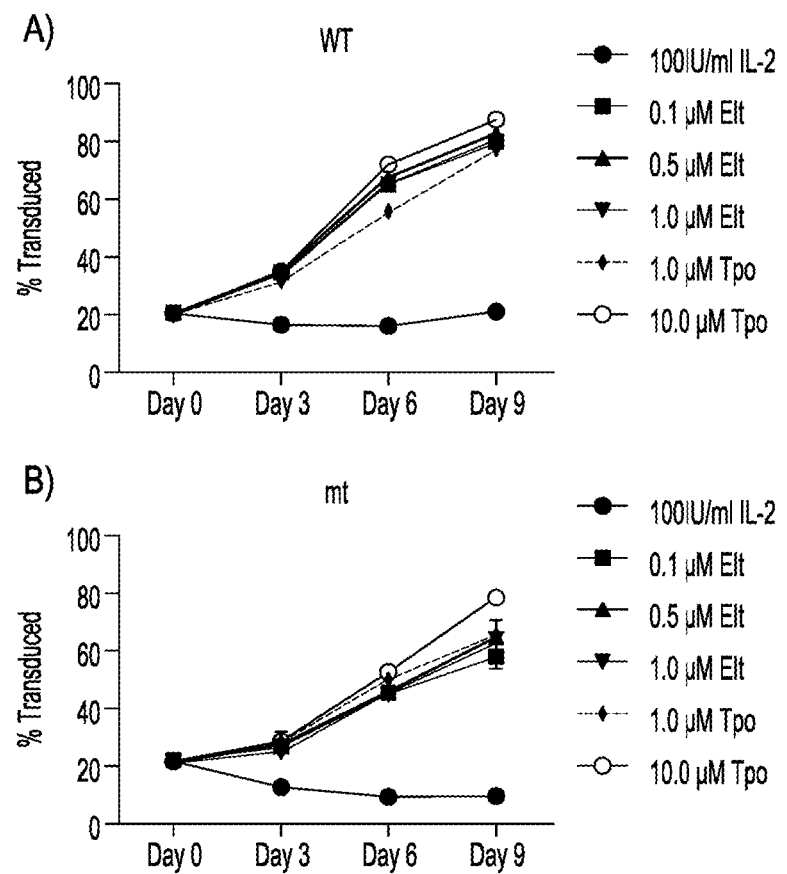

Cells harbouring either the VVT or mt TpoR responded to Eltrombopag or Tpo and the populations gradually became enriched over the course of the experiment. The responsiveness of cells harbouring the VVT receptor was above and beyond that of cells harbouring the mt receptor. 0.5 µM Eltrombopag stimulated cells enriched to 83.5% TpoR positive whereas mt cells enriched to 66.6% positive under the same conditions. In the presence of 10.0 µM Tpo WT cells enriched to 87.5% whereas mt enriched to 77.9% positive. In both cases cells stimulated with IL-2 alone did not become enriched over time (FIG. 6).

There are a number of cytokine receptors with structural similarity to TpoR which could be used to generate novel chimeric GFRs. For example, the granulocyte colony stimulating factor receptor (GCSFR), Human growth hormone receptor (HGHR) and prolactin receptor (PrlR) are all single chain and homodimeric making them ideal candidates for lentiviral gene transfer and subsequent T-cell surface expression. We therefore constructed several variations on the existing WT TpoR by replacing the intracellular domain of the TpoR with those obtained from GCSFR, HGHR or PrIR. Additionally we also created two other variants:

i) TpoR with the extracellular domain obtained from CD34 (CD34-TpoR); ii) TpoR F104S containing an extracellular point mutation which has been shown to prevent responsiveness to Thrombopoietin but not Eltrombopag (Fox et al 2010).

Lentiviral supernatants were made from each of the new variant plasmid constructs and used to directly infect the IL-3 dependent murine B-cell line Ba/F3 and primary human T-cells (FIG. 7A & B). The WT receptor was the most efficiently expressed variant in both Ba/F3 and human T-cells. The F104S mutation appeared to negatively impact on viral titres, although it still expressed at a level sufficient for experiments to be performed. The HGHR and PrIR variants both expressed to sufficient levels too. Two of the receptors tested failed to express to levels sufficient to perform subsequent experiments. The TpoR-GCSFR fusion receptor could not be detected on the surface of transduced Jurkat cells or primary human T-cells but was expressed readily upon intracellular staining suggesting that there was issues with this receptor being transported to the plasma membrane (FIG. 8). The CD34-TpoR fusion showed limited surface expression in Jurkat cells although could be detected as a clear but small population intracellularly using an anti-CD34 antibody (FIG. 8). The most likely explanation is that this receptor generates very low titre viral particles.

Initial experiments with the WT receptor used a wide range of Eltrombopag concentrations. We therefore conducted an initial experiment using WT TpoR engineered T-cells to determine a more precise concentration or range of concentrations to use for successive experiments. (FIG. 9). There was very little difference in the enrichment of TpoR+ cells over 3 and 8 days with varying concentrations of Eltrombopag, we therefore chose 0.5 μM as an optimal concentration for further experiments.

To determine whether the new variants generated were functionally active we transduced the 1L3 dependent cell line Ba/F3 and incubated the cells with either IL-3, 0.5 μM Eltrombopag or 1.0 μM Tpo and measured the proportion of cells expressing the indicated TpoR at days 3, 5 and 7. As expected the WT TpoR was able to support the enrichment of transduced cells in the presence of Eltrombopag and Tpo, the mutant F104S variant which does not bind Tpo was also able to support the enrichment of transduced cells in the presence of Eltrombopag but, as expected, had much reduced activity in response to Tpo. The TpoR-HGHR and TpoR-PrIR variants also showed functional activity in response to Eltrombopag and Tpo; however, the TpoR-PrIR variant appeared relatively unstable on the cell surface (FIG. 10) and showed less robust responses to Eltrombopag and Tpo compared with the other variants.

The WT, F104S, HGHR and PrIR variants were then tested for functional activity in primary human T-cells. Eltrombopag, but not Tpo nor IL-2, induced preferential enrichment of WT and F104S TpoR+ T-cells. Both the TpoR-HGHR and TpoR-PrIR variants also demonstrated Eltrombopag induced enrichment but the effect was not as pronounced as compared to WT or F104S (FIG. 11).

Next we aimed to determine whether the WT TpoR was functionally active in Tumour Infiltrating Lymphocytes (TIL). It was possible that the high doses of 1L2 used to generate TIL cultures could make them more dependent on 1L2 for subsequent growth. To this end we added lentiviral supernatants to melanoma TIL cultures. Cells were transduced to 65% (FIG. 12). The TILs were cultured in the presence of 200 IU/ml IL-2, or Eltrombopag or Tpo. Cells were analysed for TpoR expression at days 2 and 5. High (1 μM) but not low (0.1 μM) Tpo was able to induce enrichment of TpoR+ T-cells over the seven day period of the experiment. Moreover, both low (0.1 μM) and high (1.0 μM) dose Eltrombopag was able to induce enrichment (65% to 89% and 65% to 90% TpoR+). In contrast there was no enrichment of TpoR+ cells in the presence of IL2 supporting the notion that this is driven by signals through the TpoR.

CONCLUSION

Growth factor receptors responsive to clinically available drugs can be transferred to T-cells by gene transfer technology and therein maintain their functional capacity to deliver cell growth/survival signals. Importantly we show that as an example, TpoR engrafted primary human T-cells respond to the clinically available drug Eltrombopag and expand and survive in the absence of IL-2 which is normally required for optimal T-cell growth. The responses to Eltrombopag were not as great as those seen towards IL-2; however, there are a number of potential avenues that can be explored to optimise the growth responses. Here we initially test a truncated TpoR previously shown to enhance the responsiveness of haematopoietic stem cells to TpoR engagement (Saka et al. 2013). We show that this truncated mutant receptor was not as efficient at inducing cell growth as the WT in T-cells.

Here we tested a number of functional variants; i) an F104S extracellular mutant variant which has been previously shown to be unresponsive to Tpo; ii) a variant where the extracellular domain is replaced with human CD34; iii) three variants in which the intracellular domain is swapped for either the human growth hormone receptor (HGHR), the prolactin receptor (PrIR) or granulocyte colony stimulating factor (GCSFR). As predicted the F104S variant reduced responsiveness to Tpo, this is an important observation as it means that this variant could be safer as engineered cells would not be able to proliferate in response to circulating natural levels of Tpo but retain responsiveness to Eltrombopag. The CD34 variant expressed, however, there were some issues with viral titre which need to be resolved. Two of the three cytoplasmic domain variants functioned well (the GCSFR not expressing at the cell surface), although they showed relatively equivalent responsiveness to Eltrombopag as the WT receptor. Importantly the variants have shown how the WT receptor can be modified in attempts to improve activity.

We also demonstrate that the growth factor receptor retains activity in Tumour Infiltrating Lymphocytes (TIL). TIL are routinely grown out in the presence of very high concentrations of IL2 (up to 6000 IU/ml in some cases) and so there was a worry that these cells would be acutely dependent on IL2 for subsequent survival. Here we show that rGFR engineered TIL can be readily enriched in the presence of Eltrombopag. This opens up the possibility of using a rGFR based on the WT TpoR to engineer TIL to survive in vivo in the absence of exogenously administered IL2.

REFERENCES

Columbyova L, Loda M, Scadden DT. Cancer Res. 1995 Aug 15; 55(16):3509-12. Thrombopoietin receptor expression in human cancer cell lines and primary tissues.

Grupp S A, Kalos M, Barrett D, Aplenc R, Porter DL, Rheingold S R, Teachey D T, Chew A, Hauck B, Wright J F, Milone M C, Levine B L, June CH. N Engl J Med. 2013 Apr 18; 368(16):1509-18. Chimeric antigen receptor-modified T cells for acute lymphoid leukemia.

Erickson-Miller C L, Delorme E, Tian S S, Hopson CB, Landis A J, Valoret E L, Sellers T S, Rosen J, Miller S G, Luengo J I, Duffy K J, Jenkins J M. Stem Cells. 2009 Feb; 27(2):424-30. Preclinical activity of eltrombopag (SB-497115), an oral, nonpeptide thrombopoietin receptor agonist.

Fox N E, Lim J, Chen R, Geddis A E. Exp Hematol. 2010 May; 38(5):384-91. F104S c-Mpl responds to a transmembrane domain-binding thrombopoietin receptor agonist: proof of concept that selected receptor mutations in congenital amegakaryocytic thrombocytopenia can be stimulated with alternative thrombopoietic agents.

Kawahara M, Kimura H, Ueda H, Nagamune T. Biochem Biophys Res Commun. 2004 Feb 27; 315(1):132-8. Selection of genetically modified cell population using hapten-specific antibody/receptor chimera.

Kochenderfer J N, Dudley M E, Kassim S H, Somerville R P, Carpenter R O, Stetler-Stevenson M, Yang J C, Phan G Q, Hughes M S, Sherry R M, Raffeld M, Feldman S, Lu L, Li YF, Ngo L T, Goy A, Feldman T, Spaner D E, Wang M L, Chen C C, Kranick S M, Nath A, Nathan D A, Morton K E, Toomey M A, Rosenberg S A. J Clin Oncol. 2015 33(6):540-9. Chemotherapy-refractory diffuse large B-cell lymphoma and indolent B-cell malignancies can be effectively treated with autologous T cells expressing an anti-CD19 chimeric antigen receptor.

Jin L, Zeng H, Chien S, Otto K G, Richard R E, Emery D W, Blau C A. Nat Genet. 2000 Sep; 26(1):64-6. In vivo selection using a cell-growth switch.

Kawahara M, Chen J, Sogo T, Teng J, Otsu M, Onodera M, Nakauchi H, Ueda H, Nagamune T. Cytokine. 2011 Sep; 55(3):402-8. Growth promotion of genetically modified hematopoietic progenitors using an antibody/c-Mpl chimera.

Morgan R A, Dudley M E, Wunderlich J R, Hughes M S, Yang J C, Sherry R M, Royal R E, Topalian SL, Kammula U S, Restifo N P, Zheng Z, Nahvi A, de Vries CR, Rogers-Freezer U, Mavroukakis SA, Rosenberg SA. Science. 2006 Oct 6; 314(5796):126-9. Cancer regression in patients after transfer of genetically engineered lymphocytes.

Nagashima T, Ueda Y, Hanazono Y, Kume A, Shibata H, Ageyama N, Terao K, Ozawa K, Hasegawa M. J Gene Med. 2004 Jan; 6(1):22-31. In vivo expansion of gene-modified hematopoietic cells by a novel selective amplifier gene utilizing the erythropoietin receptor as a molecular switch.

Rapoport A P, Stadtmauer E A, Binder-Scholl G K, Goloubeva O, Vogl D T, Lacey S F, Badros A Z, Garfall A, Weiss B, Finklestein J, Kulikovskaya I, Sinha S K, Kronsberg S, Gupta M, Bond S, Melchiori L, Brewer J E, Bennett A D, Gerry A B, Pumphrey N J, Williams D, Tayton-Martin H K, Ribeiro L, Holdich T, Yanovich S, Hardy N, Yared J, Kerr N, Philip S, Westphal S, Siegel D L, Levine B L, Jakobsen B K, Kalos M, June C H. Nat Med. 2015 Aug; 21(8):914-21. NY-ESO-1-specific TCR-engineered T cells mediate sustained antigen-specific antitumor effects in myeloma.

Richard R E, Wood B, Zeng H, Jin L, Papayannopoulou T, Blau CA. Blood. 2000 Jan 15; 95(2):430-6. Expansion of genetically modified primary human hemopoietic cells using chemical inducers of dimerization.

Rosenberg S A, Yang J C, Sherry R M, Kammula U S, Hughes M S, Phan G Q, Citrin D E, Restifo N P, Robbins P F, Wunderlich J R, Morton K E, Laurencot C M, Steinberg S M, White D E, Dudley M E. Clin Cancer Res. 2011 Jul 1; 17(13):4550-7. Durable complete responses in heavily pretreated patients with metastatic melanoma using T-cell transfer immunotherapy.

Saka K, Kawahara M, Teng J, Otsu M, Nakauchi H, Nagamune T. J Biotechnol. 2013 Dec; 168(4):659-65. Top-down motif engineering of a cytokine receptor for directing ex vivo expansion of hematopoietic stem cells.

Saka K, Kawahara M, Ueda H, Nagamune T. Biotechnol Bioeng. 2012 Jun; 109(6):1528-37. Activation of target signal transducers utilizing chimeric receptors with signaling-molecule binding motifs.

Yamane N, Tanaka Y, Ohyabu N, Yamane S, Maekawa K, Ishizaki J, Suzuki R, Itoh T, Takemoto H. EurJ Pharmacol. 2008 May 31; 586(1-3):44-51. Characterization of novel non-peptide thrombopoietin mimetics, their species specificity and the activation mechanism of the thrombopoietin receptor.

The invention claimed is:

1. A T or natural killer (NK) cell comprising a recombinant thrombopoietin receptor (TpoR) comprising:
   (i) a thrombopoietin receptor extracellular (EC) domain,
   (ii) a thrombopoietin receptor transmembrane (TM) domain, and
   (iii) an intracellular (IC) domain;
   wherein the IC domain is from a human growth hormone receptor or a human prolactin receptor.

2. The T or NK cell of claim 1 wherein binding of a ligand to the TpoR induces proliferation of the T or NK cell.

3. The T or NK cell of claim 2 wherein the ligand is human thrombopoietin or a thrombopoietin receptor agonist.

4. The T or NK cell of claim 3 wherein the thrombopoietin receptor agonist binds to the TM domain.

5. The T or NK cell of claim 3 wherein the thrombopoietin receptor agonist is selected from Eltrombopag or Romiplostim.

6. The T or NK cell of claim 1 having the TM sequence of SEQ ID NO:3 or a variant thereof having at least 95% sequence identity to SEQ ID NO:3 which binds a thrombopoietin receptor agonist.

7. The T or NK cell of claim 1, wherein the IC domain comprises the sequence of SEQ ID NO:4 or a variant thereof having at least 95% sequence identity to SEQ ID NO:4.

8. The T or NK cell of claim 1, wherein the TM domain comprises the sequence of SEQ ID NO:3 or a variant thereof having at least 95% sequence identity to SEQ ID NO:3, and wherein the IC domain comprises the sequence of SEQ ID NO:4 or a variant thereof having at least 95% sequence identity to SEQ ID NO:4.

9. The T or NK cell of claim 1 which comprises the sequence of SEQ ID NO:8 or 9, or a variant thereof having at least 95% sequence identity to SEQ ID NO: 8 or 9 but retains the capacity to i) bind to human thrombopoietin or a human thrombopoietin receptor and ii) induce cell proliferation or survival.

10. The T cell or NK cell of claim 1, wherein the EC domain does not have a growth factor binding function and the TM domain binds to Eltrombopag.

11. The T cell or NK cell of claim 1, wherein the T cell is selected from a Tumour Infiltrating Lymphocyte (TIL), a T Regulatory Cell (Treg) or a primary T cell.

12. The T cell or NK cell of claim 1, further comprising a recombinant T-cell receptor (TCR) and/or Chimeric Antigen Receptor (CAR).

13. A nucleic acid encoding a recombinant thrombopoietin receptor (TpoR) comprising:
   (i) a thrombopoietin receptor extracellular (EC) domain,
   (ii) a thrombopoietin receptor transmembrane (TM) domain, and
   (iii) an intracellular (IC) domain;
   wherein the IC domain is from a human growth hormone receptor or a human prolactin receptor.

14. A vector comprising the nucleic acid of claim 13.

15. A method of making the T or NK cell of claim 1 comprising a step of introducing the nucleic acid of claim 13, or the vector of claim 14, into a T or NK cell.

16. A pharmaceutical composition comprising the T or NK cell of claim 1, or the vector of claim 14, together with a pharmaceutically acceptable carrier, diluent or excipient.

17. A method of in vivo cell expansion comprising:
   administering the T or NK cell of claim 1, or the vector of claim 14, to a subject; and
   administering thrombopoietin or a thrombopoietin receptor agonist to the subject.

18. A method of adoptive cell therapy comprising administering the T or NK cell of claim 1, or the vector of claim 14, to a subject in need thereof.

19. A method of treating cancer comprising a step of administering the T or NK cell of claim 1 to a subject in need thereof.

20. The method of claim 18 comprising administering an effective amount of Eltrombopag to the subject.

21. A method of in vitro or ex vivo expansion of the T or NK cell of claim 1 comprising contacting the T or NK cell of claim 1 with Eltrombopag.

22. A method of treating a cancer comprising administering a composition comprising the T or NK cell of claim 1 in combination with thrombopoietin or a thrombopoietin receptor agonist.

* * * * *